(12) United States Patent
Dong et al.

(10) Patent No.: US 7,368,427 B1
(45) Date of Patent: May 6, 2008

(54) GLP-1 ANALOGUES

(75) Inventors: Zheng Xin Dong, Holliston, MA (US); David H. Coy, New Orleans, LA (US)

(73) Assignees: Societe de Conseils de Recherches et d'Applications Scientifiques, SAS, Paris (FR); The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 09/856,676

(22) PCT Filed: Dec. 7, 1999

(86) PCT No.: PCT/US99/28929

§ 371 (c)(1),
(2), (4) Date: Jul. 16, 2001

(87) PCT Pub. No.: WO00/34332

PCT Pub. Date: Jun. 15, 2000

(51) Int. Cl.
*A61K 38/26* (2006.01)
*C07K 14/605* (2006.01)
(52) U.S. Cl. .................. 514/12; 530/324; 530/308
(58) Field of Classification Search ............ 514/12; 530/324
See application file for complete search history.

(56) References Cited

U.S. PATENT DOCUMENTS

| 5,545,618 A | 8/1996 | Buckley et al. |
| 5,705,483 A | 1/1998 | Galloway et al. |
| 6,410,513 B1 | 6/2002 | Galloway et al. |
| 6,458,924 B2 | 10/2002 | Knudsen et al. |
| 6,620,910 B1 | 9/2003 | Calas et al. |
| 6,720,407 B1 | 4/2004 | Hughes et al. |
| 6,903,186 B1 | 6/2005 | Dong et al. |

FOREIGN PATENT DOCUMENTS

| EP | 0 733 644 A | 9/1996 |
| FR | 2 777 283 A | 10/1999 |
| WO | WO91 11457 A | 8/1991 |
| WO | WO97 29180 A | 8/1997 |
| WO | WO98 08871 A | 3/1998 |
| WO | 98/19698 | 5/1998 |
| WO | 99/43705 | 9/1999 |
| WO | 00/34331 | 6/2000 |
| WO | 01/035988 | 5/2001 |

OTHER PUBLICATIONS

Mojsov, S. "Structural requirements for biological activity of glucagon-like peptide I," Int. J. Pep. Prot. Res., 1992, 40:333-343.

*Primary Examiner*—Michael Borin
(74) *Attorney, Agent, or Firm*—Fish & Richardson; Alan F. Feeney; Tony K. Uhm

(57) ABSTRACT

The present invention is directed to peptide analogues of glucagon-like peptide-1, the pharmaceutically-acceptable salts thereof, to methods of using such analogues to treat mammals and to pharmaceutical compositions useful therefor comprising said analogues.

3 Claims, No Drawings

GLP-1 ANALOGUES

BACKGROUND OF THE INVENTION

The present invention is directed to peptide analogues of glucagon-like peptide-1, the pharmaceutically-acceptable salts thereof, to methods of using such analogues to treat mammals and to pharmaceutical compositions useful therefor comprising said analogues.

Glucagon-like peptide-1 (7-36) amide (GLP-1) (SEQ ID NO: 1) is synthesized in the intestinal L-cells by tissue-specific post-translational processing of the glucagon precursor pre-proglucagon (Varndell, J. M., et al., J. Histochem Cytochem, 1985:33:1080-6) and is released into the circulation in response to a meal. The plasma concentration of GLP-1 rises from a fasting level of approximately 15 pmol/L to a peak postprandial level of 40 pmol/L. It has been demonstrated that, for a given rise in plasma glucose concentration, the increase in plasma insulin is approximately threefold greater when glucose is administered orally compared with intravenously (Kreymann, B., et al., Lancet 1987:2, 1300-4). This alimentary enhancement of insulin release, known as the incretin effect, is primarily humoral and GLP-1 is now thought to be the most potent physiological incretin in humans. In addition to the insulinotropic effect, GLP-1 suppresses glucagon secretion, delays gastric emptying (Wettergren A., et al., Dig Dis Sci 1993:38:665-73) and may enhance peripheral glucose disposal (D'Alessio, D. A. et al., J. Clin Invest 1994:93:2293-6).

In 1994, the therapeutic potential of GLP-1 was suggested following the observation that a single subcutaneous (s/c) dose of GLP-1 could completely normalize postprandial glucose levels in patients with non-insulin-dependent diabetes mellitus (NIDDM) (Gutniak, M. K., et al., Diabetes Care 1994:17:1039-44). This effect was thought to be mediated both by increased insulin release and by a reduction in glucagon secretion. Furthermore, an intravenous infusion of GLP-1 has been shown to delay postprandial gastric emptying in patients with NIDDM (Williams, B., et al., J. Clin Endo Metab 1996:81:327-32). Unlike sulfonylureas, the insulinotropic action of GLP-1 is dependent on plasma glucose concentration (Holz, G. G. 4th, et al., Nature 1993: 361:362-5). Thus, the loss of GLP-1-mediated insulin release at low plasma glucose concentration protects against severe hypoglycemia. This combination of actions gives GLP-1 unique potential therapeutic advantages over other agents currently used to treat NIDDM.

Numerous studies have shown that when given to healthy subjects, GLP-1 potently influences glycemic levels as well as insulin and glucagon concentrations (Orskov, C, Diabetologia 35:701-711, 1992; Holst, J. J., et al., *Potential of GLP-1 in diabetes management* in Glucagon III, Handbook of Experimental Pharmacology, Lefevbre P J, Ed. Berlin, Springer Verlag, 1996, p. 311-326), effects which are glucose dependent (Kreymann, B., et al., Lancet ii: 1300-1304, 1987; Weir, G. C., et al., Diabetes 38:338-342, 1989). Moreover, it is also effective in patients with diabetes (Gutniak, M., N. Engl J Med 226:1316-1322, 1992; Nathan, D. M., et al., Diabetes Care 15:270-276, 1992), normalizing blood glucose levels in type 2 diabetic subjects (Nauck, M. A., et al., Diagbetologia 36:741-744, 1993), and improving glycemic control in type 1 patients (Creutzfeldt, W. O., et al., Diabetes Care 19:580-586, 1996), raising the possibility of its use as a therapeutic agent.

GLP-1 is, however, metabolically unstable, having a plasma half-life ($t_{1/2}$) of only 1-2 min in vivo. Exogenously administered GLP-1 is also rapidly degraded (Deacon, C. F., et al., Diabetes 44:1126-1131, 1995). This metabolic instability limits the therapeutic potential of native GLP-1. Hence, there is a need for GLP-1 analogues that are more active or are more metabolically stable than native GLP-1.

SUMMARY OF THE INVENTION

In one aspect, the present invention is directed to a compound of formula (I),

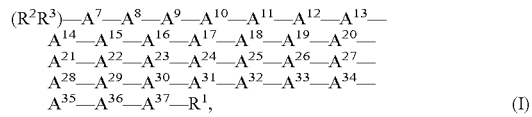

$$(R^2R^3)-A^7-A^8-A^9-A^{10}-A^{11}-A^{12}-A^{13}-$$
$$A^{14}-A^{15}-A^{16}-A^{17}-A^{18}-A^{19}-A^{20}-$$
$$A^{21}-A^{22}-A^{23}-A^{24}-A^{25}-A^{26}-A^{27}-$$
$$A^{28}-A^{29}-A^{30}-A^{31}-A^{32}-A^{33}-A^{34}-$$
$$A^{35}-A^{36}-A^{37}-R^1, \quad (I)$$

wherein
$A^7$ is L-His, Ura, Paa, Pta, D-His, Tyr, 3-Pal, 4-Pal, Hppa, Tma-His, Amp or deleted, provided that when $A^7$ is Ura, Paa, Pta or Hppa then $R^2$ and $R^3$ are deleted;
$A^8$ is Ala, D-Ala, Aib, Acc, N-Me-Ala, N-Me-D-Ala, Arg or N-Me-Gly;
$A^9$ is Glu, N-Me-Glu, N-Me-Asp or Asp;
$A^{10}$ is Gly, Acc, Ala, D-Ala, Phe or Aib;
$A^{11}$ is Thr or Ser;
$A^{12}$ is Phe, Acc, Aic, Aib, 3-Pal, 4-Pal, β-Nal, Cha, Trp or $X^1$-Phe;
$A^{13}$ is Thr or Ser;
$A^{14}$ is Ser, Thr, Ala or Aib;
$A^{15}$ is Asp, Ala, D-Asp or Glu;
$A^{16}$ is Val, D-Val, Acc, Aib, Leu, Ile, Tle, Nle, Abu, Ala, D-Ala, Tba or Cha;
$A^{17}$ is Ser, Ala, D-Ala, Aib, Acc or Thr;
$A^{18}$ is Ser, Ala, D-Ala, Aib, Acc or Thr;
$A^{19}$ is Tyr, D-Tyr, Cha, Phe, 3-Pal, 4-Pal, Acc, β-Nal, Amp or $X^1$-Phe;
$A^{20}$ is Leu, Ala, Acc, Aib, Nle, Ile, Cha, Tle, Val, Phe or $X^1$-Phe;
$A^{21}$ is Glu, Ala or Asp;
$A^{22}$ is Gly, Acc, Ala, D-Ala, β-Ala or Aib;
$A^{23}$ is Gln, Asp, Ala, D-Ala, Aib, Acc, Asn or Glu;
$A^{24}$ is Ala, Aib, Val, Abu, Tle or Acc;
$A^{25}$ is Ala, Aib, Val, Abu, Tle, Acc, Lys, Arg, hArg, Orn, HN—CH(($CH_2)_n$—NR$^{10}$R$^{11}$)—C(O) or HN—CH(($CH_2)_e$—X$^3$)—C(O);
$A^{26}$ is Lys, Ala, 3-Pal, 4-Pal, Arg, hArg, Orn, Amp, HN—CH(($CH_2)_n$—NR$^{10}$R$^{11}$)—C(O) or HN—CH(($CH_2)_e$—X$^3$)—C(O);
$A^{27}$ is Glu, Ala, D-Ala or Asp;
$A^{28}$ is Phe, Ala, Pal, β-Nal, $X^1$-Phe, Aic, Acc, Aib, Cha or Trp;
$A^{29}$ is Ile, Acc, Aib, Leu, Nle, Cha, Tle, Val, Abu, Ala, Tba or Phe;
$A^{30}$ is Ala, Aib, Acc or deleted;
$A^{31}$ is Trp, Ala, β-Nal, 3-Pal, 4-Pal, Phe, Acc, Aib, Cha, Amp or deleted;
$A^{32}$ is Leu, Ala, Acc, Aib, Nle, Ile, Cha, Tle, Phe, $X^1$-Phe, Ala or deleted;
$A^{33}$ is Val, Acc, Aib, Leu, Ile, Tle, Nle, Cha, Ala, Phe, Abu, $X^1$-Phe, Tba, Gaba or deleted;
$A^{34}$ is Lys, Arg, hArg, Orn, Amp, Gaba, HN—CH(($CH_2)_n$—NR$^{10}$R$^{11}$)—C(O), NH—CH(($CH_2)_3$—X$^3$)—C(O) or deleted;
$A^{35}$ is Gly or deleted;
$A^{36}$ is L- or D-Arg, D- or L-Lys, D- or L-hArg, D- or L-Orn, Amp, HN—CH(($CH_2)_n$—NR$^{10}$R$^{11}$)—C(O), HN—CH(($CH_2)_e$—X$^3$)—C(O) or deleted;
$A^{37}$ is Gly or deleted;

X$^1$ for each occurrence is independently selected from the group consisting of (C$_1$-C$_6$)alkyl, OH and halo;

R$^1$ is OH, NH$_2$, (C$_1$-C$_{12}$)alkoxy, or NH—X$^2$—CH$_2$—Z$^0$, wherein X$^2$ is a (C$_1$-C$_{12}$)hydrocarbon moiety, and Z$^0$ is H, OH, CO$_2$H or CONH$_2$;

X$^3$ is

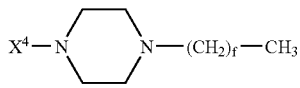

or —C(O)—NHR$^{12}$, wherein X$^4$ for each occurrence is independently —C(O)—, —NH—C(O)— or —CH$_2$—, and f for each occurrence is independently an integer from 1 to 29;

each of R$^2$ and R$^3$ is independently selected from the group consisting of H, (C$_1$-C$_{30}$)alkyl, (C$_2$-C$_{30}$)alkenyl, phenyl(C$_1$-C$_{30}$)alkyl, naphthyl(C$_1$-C$_{30}$)alkyl, hydroxy(C$_1$-C$_{30}$)alkyl, hydroxy(C$_2$-C$_{30}$)alkenyl, hydroxyphenyl(C$_1$-C$_{30}$)alkyl, and hydroxynaphthyl (C$_1$-C$_{30}$)alkyl; or one of R$^2$ and R$^3$ is C(O)X$^5$ in which X$^5$ is (C$_1$-C$_{30}$)alkyl, (C$_2$-C$_{30}$)alkenyl, phenyl (C$_1$-C$_{30}$)alkyl, naphthyl(C$_1$-C$_{30}$)alkyl, hydroxy(C$_1$-C$_{30}$)alkyl, hydroxy(C$_2$-C$_{30}$)alkenyl, hydroxyphenyl (C$_1$-C$_{30}$)alkyl, hydroxynaphthyl(C$_1$-C$_{30}$)alkyl,

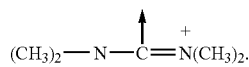

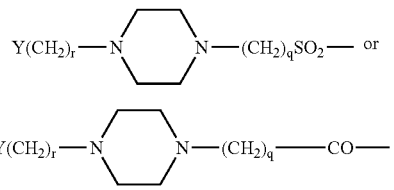

where Y is H or OH, r is 0-4 and q is 0-4;

n for each occurrence is independently an integer from 1-5; and

R$^{10}$ and R$^{11}$ for each occurrence is each independently H, (C$_1$-C$_{30}$)alkyl, (C$_1$-C$_{30}$)acyl, (C$_1$-C$_{30}$)alkylsulfonyl, —C((NH)(NH$_2$)) or

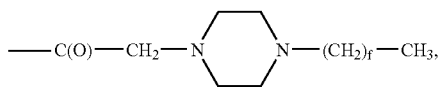

provided that when R$^{10}$ is (C$_1$-C$_{30}$acyl), (C$_1$-C$_{30}$)alkylsulfonyl, —C((NH)(NH$_2$)) or

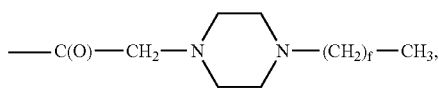

R$^{11}$ is H or (C$_1$-C$_{30}$)alkyl; and
R$^{12}$ is (C$_1$-C$_{30}$)alkyl;

with the proviso that:
(i) at least one amino acid of a compound of formula (I) is not the same as the native sequence of hGLP-1(7-36, or -37)NH$_2$ (SEQ ID NOS: 1, 2) or hGLP-1(7-36, or -37)OH (SEQ ID NOS: 3, 4);

(ii) a compound of formula (I) is not an analogue of hGLP-1(7-36, or -37)NH$_2$ (SEQ ID NOS: 1, 2) or hGLP-1(7-36, or -37)OH (SEQ ID NOS: 3, 4) wherein a single position has been substituted by Ala;

(iii) a compound of formula (I) is not [Lys$^{26}$(N$^\epsilon$-alkanoyl)]hGLP-1(7-36, or -37)-E (SEQ ID NOS: 5-8), [Lys$^{34}$(N$^\epsilon$-alkanoyl)]hGLP-1(7-36, or -37)-E (SEQ ID NOS: 9-12), [Lys$^{26,34}$-bis(N$^\epsilon$-alkanoyl)]hGLP-1(7-36, or -37)-E (SEQ ID NOS: 13-16), [Arg$^{26}$, Lys$^{34}$(N$^\epsilon$-alkanoyl)]hGLP-1(8-36, or -37)-E (SEQ ID NOS: 17-20), or [Arg$^{26,34}$, Lys$^{36}$(N$^\epsilon$-alkanoyl)]hGLP-1(7-36, or -37)-E, wherein E is —OH or —NH$_2$ (SEQ ID NOS: 21-24);

(iv) a compound of formula (I) is not Z$^1$-hGLP-1(7-36, or -37)-OH, Z$^1$-hGLP-1(7-36, or -37)-NH$_2$, where Z$^1$ is selected from the group consisting of
(a) [Arg$^{26}$] (SEQ ID NOS: 25-28), [Arg$^{34}$] (SEQ ID NOS: 29-32), [Arg$^{26,34}$] (SEQ ID NOS: 33-36), [Lys$^{36}$] (SEQ ID NOS: 37-40), [Arg$^{26}$, Lys$^{36}$] (SEQ ID NOS: 41-44), [Arg$^{34}$, Lys$^{36}$] (SEQ ID NOS: 45-48), [D-Lys$^{36}$], [Arg$^{36}$] (SEQ ID NOS: 3,4,1,2), [D-Arg$^{36}$], [Arg$^{26,34}$, Lys$^{36}$] (SEQ ID NOS: 49-52), or [Arg$^{26,38}$, Lys$^{34}$] (SEQ ID NOS: 25-28);
(b) [Asp$^{21}$] (SEQ ID NOS: 53-56);
(c) at least one of [Aib$^8$] (SEQ ID NOS: 57-60), [D-Ala$^8$] and [Asp$^9$] (SEQ ID NOS: 61-64); and
(d) [Tyr$^7$] (SEQ ID NOS: 65-68), [N-acyl-His$^7$] (SEQ ID NOS: 69-72), [N-alkyl-His$^7$], [N-acyl-D-His$^7$] (SEQ ID NOS: 73-76) or [N-alkyl-D-His$^7$];

(v) a compound of formula (I) is not a combination of any two of the substitutions listed in groups (a) to (d); and (vi) a compound of formula (I) is not [N-Me-Ala$^8$]hGLP-1(8-36 or -37) (SEQ ID NOS: 75, 78), [Glu$^{15}$]hGLP-1(7-36 or -37) (SEQ ID NOS: 79, 80), [Asp$^{21}$]hGLP-1(7-36 or -37) (SEQ ID NOS: 53, 54) or [Phe$^{31}$]hGLP-1(7-36 or -37) (SEQ ID NOS: 81, 82).

A preferred compound of the immediately foregoing compound of formula (I) is where A$^{11}$ is Thr; A$^{13}$ is Thr; A$^{14}$ is Ser, Aib or Ala; A$^{17}$ is Ser, Ala, Aib or D-Ala; A$^{18}$ is Ser, Ala, Aib or D-Ala; A$^{21}$ is Glu or Ala; A$^{23}$ is Gln, Glu, or Ala; and A$^{27}$ is Glu or Ala; or a pharmaceutically acceptable salt thereof.

A preferred compound of the immediately foregoing compound of formula (I) is where A$^9$ is Glu, N-Me-Glu or N-Me-Asp; A$^{12}$ is Phe, Acc or Aic; A$^{16}$ is Val, D-Val, Acc, Aib, Ala, Tle or D-Ala; A$^{19}$ is Tyr, 3-Pal, 4-Pal or D-Tyr; A$^{20}$ is Leu, Acc, Cha, Ala or Tle; A$^{24}$ is Ala, Aib or Acc; A$^{25}$ is Ala, Aib, Acc, Lys, Arg, hArg, Orn, HN—CH((CH$_2$)$_n$—NH—R$^{10}$)—C(O); A$^{28}$ is Phe or Ala; A$^{29}$ is Ile, Acc or Tle; A$^{30}$ is Ala, Aib or deleted; A$^{31}$ is Trp, Ala, 3-Pal, 4-Pal or deleted; A$^{32}$ is Leu, Acc, Cha, Ala or deleted; A$^{33}$ is Val, Acc, Ala, Gaba, Tle or deleted; or a pharmaceutically acceptable salt thereof.

A preferred compound of the immediately foregoing compound of formula (I) is where A$^8$ is Ala, D-Ala, Aib, A6c, A5c, N-Me-Ala, N-Me-D-Ala or N-Me-Gly; A$^{10}$ is Gly, Ala, D-Ala or Phe; A$^{12}$ is Phe, A6c or A5c; A$^{16}$ is Val, Ala, Tle, A6c, A5c or D-Val; A$^{20}$ is Leu, A6c, A5c, Cha, Ala or Tle; A$^{22}$ is Gly, Aib, β-Ala, L-Ala or D-Ala; A$^{24}$ is Ala or Aib; A$^{29}$ is Ile, A6c, A5c or Tle; A$^{32}$ is Leu, A6c, A5c, Cha, Ala or deleted; A$^{33}$ is Val, A6c, A5c, Ala, Gaba, Tle or deleted; or a pharmaceutically acceptable salt thereof.

A preferred compound of the immediately foregoing compound of formula (I) is where $R^1$ is OH or $NH_2$ or a pharmaceutically acceptable salt thereof.

A preferred compound of the immediately foregoing compound of formula (I) or a pharmaceutically acceptable salt thereof is where $R^2$ is H and $R^3$ is $(C_1-C_{30})$alkyl, $(C_2-C_{30})$alkenyl, $(C_1-C_{30})$acyl,

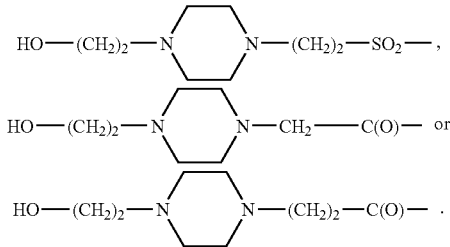

A most preferred compound of formula (I) is where said compound is [D-Ala$^8$, Ala$^{17,22,23,27}$, 3-Pal$^{19,31}$, Gaba$^{34}$]-GLP-1(7-34)NH$_2$; [D-Ala$^{8,23,27}$, 3-Pal$^{19,31}$]hGLP-1(7-35)-NH$_2$; [Ala$^{18,23,27}$, 3-Pal$^{19,31}$]hGLP-1(7-35)-NH$_2$ (SEQ ID NO: 83); [Ala$^{16,23,27}$, 3-Pal$^{19,31}$]hGLP-1(7-35)-NH$_2$ (SEQ ID NO: 84); [Ala$^{14,23,27}$, 3-Pal$^{19,31}$]hGLP-1(7-35)-NH$_2$ (SEQ ID NO: 85); [Ala$^{22,23,27}$, 3-Pal$^{19,31}$]hGLP-1(7-35)-NH$_2$ (SEQ ID NO: 86); [Hppa$^7$]hGLP-1(7-36)-NH$_2$ (SEQ ID NO: 87); [Ala$^{15,23,27}$, 3-Pal$^{19,31}$]hGLP-1(7-35)-NH$_2$ (SEQ ID NO: 88); [Ala$^{17,23,27}$, 3-Pal$^{19,31}$]hGLP-1(7-35)-NH$_2$ (SEQ ID NO: 89); [Ala$^{22,23,27}$, 3-Pal$^{19,31}$, Gaba$^{34}$]hGLP-1(7-34)-NH$_2$ (SEQ ID NO: 90); [Ala$^{15,22,23,27}$, 3-Pal$^{19,31}$, Gaba$^{34}$]hGLP-1(7-34)-NH$_2$ (SEQ ID NO: 91); [Ala$^{17,22,23,27}$, 3-Pal$^{19,31}$, Gaba$^{34}$]hGLP-1(7-34)-NH$_2$ (SEQ ID NO: 92); [Ala$^{18,22,23,27}$, 3-Pal$^{19,31}$, Gaba$^{34}$]hGLP-1(7-34)-NH$_2$ (SEQ ID NO: 93); [Ala$^{21,22,23,27}$, 3-Pal$^{19,31}$, Gaba$^{34}$]hGLP-1(7-34)-NH$_2$ (SEQ ID NO: 94); [Ala$^{22,23,26,27}$, 3-Pal$^{19,31}$, Gaba$^{34}$]hGLP-1(7-34)-NH$_2$ (SEQ ID NO: 95); [Ala$^{22,23,27,32}$, 3-Pal$^{19,31}$, Gaba$^{34}$]hGLP-1(7-34)-NH$_2$ (SEQ ID NO: 96); [Ala$^{22,23,26,27}$, 3-Pal$^{19,31}$, Gaba$^{33}$]hGLP-1(7-33)-NH$_2$ (SEQ ID NO: 97); [Ala$^{22,23,27,31}$, 3-Pal$^{19}$, Gaba$^{33}$]hGLP-1(7-33)-NH$_2$ (SEQ ID NO: 98); [Ala$^{22,23,27,28}$, 3-Pal$^{19,31}$, Gaba$^{33}$]hGLP-1(7-33)-NH$_2$ (SEQ ID NO: 99); [Ala$^{22,23,27,29}$, 3-Pal$^{19,31}$, Gaba$^{33}$]hGLP-1(7-33)-NH$_2$ (SEQ ID NO: 100); [Ala$^{23,27}$, 3-Pal$^{19,31}$, Gaba$^{33}$]hGLP-1(7-33)-NH$_2$ (SEQ ID NO: 101); [Ala$^{20,22,23,27}$, 3-Pal$^{19,31}$, Gaba$^{33}$]hGLP-1(7-33)-NH$_2$ (SEQ ID NO: 102); [Ala$^{22,23,27}$, 3-Pal$^{19,31}$, Gaba$^{33}$]hGLP-1(7-33)-NH$_2$ (SEQ ID NO: 103); [Ala$^{17,22,23,27}$, 3-Pal$^{19,31}$, Gaba$^{33}$]hGLP-1(7-33)-NH$_2$ (SEQ ID NO: 104); [D-Ala$^{10}$, Ala$^{22,23,27}$, 3-Pal$^{19,31}$, Gaba$^{33}$]hGLP-1(7-33)-NH$_2$; [D-Ala$^8$, Ala$^{17,23,27}$, 3-Pal$^{19,31}$]hGLP-1(7-34)-NH$_2$; [Ala$^{17,23,27}$, 3-Pal$^{19,26,31}$]hGLP-1(7-34)-NH$_2$ (SEQ ID NO: 105); [D-Ala$^8$, Ala$^{17}$, 3-Pal$^{19,31}$]hGLP-1(7-34)-NH$_2$; [Ala$^{17,23,27}$, 3-Pal$^{19,31}$]hGLP-1(7-34)-NH$_2$ (SEQ ID NO: 106); [D-Ala$^8$, Ala$^{17,23,27}$, 3-Pal$^{19,31}$, Tle$^{29}$]hGLP-1(7-34)-NH$_2$; [D-Ala$^8$, Ala$^{17,23,27}$, 3-Pal$^{19,31}$, Tle$^{16}$]hGLP-1(7-34)-NH$_2$; [D-Ala$^8$, Ala$^{17,23,27}$, 3-Pal$^{19,31}$, Gaba$^{34}$]hGLP-1(7-34)-NH$_2$; [D-Ala$^{22}$, Ala$^{17,23,27}$, 3-Pal$^{19,31}$, Gaba$^{34}$]hGLP-1(7-34)-NH$_2$; [Aib$^8$, Ala$^{17,23,27}$, 3-Pal$^{19,31}$, Gaba$^{34}$]hGLP-1(7-34)-NH$_2$ (SEQ ID NO: 107); [D-Ala$^8$, Ala$^{17,22,23,27}$, 3-Pal$^{19,31}$]hGLP-1(7-33)-NH$_2$; [Aib$^8$, Ala$^{17,22,23,27}$, 3-Pal$^{19,31}$]hGLP-1(7-33)-NH$_2$ (SEQ ID NO: 108); [Ala$^{17,18,23,27}$, 3-Pal$^{19,31}$, Gaba$^{34}$]hGLP-1(7-34)-NH$_2$ (SEQ ID NO: 109); [Ala$^{17,23,27}$, 3-Pal$^{19,31}$, Tle$^{33}$, Gaba$^{34}$]hGLP-1(7-34)-NH$_2$ (SEQ ID NO: 110); [Tle$^{16}$, Ala$^{17,23,27}$, 3-Pal$^{19,31}$, Gaba$^{34}$]hGLP-1(7-34)-NH$_2$ (SEQ ID NO: 111); [N-Me-D-Ala$^8$, Ala$^{17,22,23,27}$, 3-Pal$^{19,31}$]hGLP-1(7-33)-NH$_2$; [Aib$^8$, Ala$^{17,18,22,23,27}$, 3-Pal$^{19,31}$]hGLP-1(7-33)-NH$_2$ (SEQ ID NO: 112); [Ala$^{17,18,22,23,27}$, 3-Pal$^{19,31}$, Tle$^{16,20}$, Gaba$^{34}$]hGLP-1(7-34)-NH$_2$ (SEQ ID NO: 113); [D-Ala$^8$, Ala$^{17,18,22,23,27}$, 3-Pal$^{19,31}$, Tle$^{16}$, Gaba$^{34}$]hGLP-1(7-34)-NH$_2$; [D-Ala$^{8,22}$, Ala$^{17,18,23,27}$, 3-Pal$^{19,31}$, Gaba$^{34}$]hGLP-1(7-34)-NH$_2$; [D-Ala$^{8,18}$, Ala$^{17,22,23,27}$, 3-Pal$^{19,31}$, Gaba$^{34}$]hGLP-1(7-34)-NH$_2$; [D-Ala$^{8,17}$, Ala$^{18,22,23,27}$, 3-Pal$^{19,31}$, Gaba$^{34}$]hGLP-1(7-34)-NH$_2$; or [D-Ala$^8$, Ala$^{17,18,22,23,27}$, 3-Pal$^{19,31}$, Gaba$^{34}$]hGLP-1(7-34)-NH$_2$; or a pharmaceutically acceptable salt thereof.

Another most preferred compound of formula (I) is wherein said compound is [Aib$^8$, A6c$^{32}$]hGLP-1(7-36)NH$_2$ (SEQ ID NO: 114); [A6c$^{20,32}$]hGLP-1(7-36)-NH$_2$ (SEQ ID NO: 115); [Aib$^8$]hGLP-1(7-36)-NH$_2$ (SEQ ID NO: 116); [(Tma-His)$^7$]hGLP-1(7-36)-NH$_2$ (SEQ ID NO: 117); [A6c$^8$]hGLP-1(8-36)-NH$_2$ (SEQ ID NO: 118); [A6c$_8$]hGLP-1(7-36)-NH$_2$ (SEQ ID NO: 119); [A6c$^{16,20}$]hGLP-1(7-36)-NH$_2$ (SEQ ID NO: 120); [A6c$^{29,32}$]hGLP-1(7-36)-NH$_2$ (SEQ ID NO: 121); [A6c$^{20}$, Aib$^{24}$]hGLP-1(7-36)-NH$_2$ (SEQ ID NO: 122); [Aib$^{24}$, A6c$^{29,32}$]hGLP-1(7-36)-NH$_2$ (SEQ ID NO: 123); [A6c$^{16,29,32}$]hGLP-1(7-36)-NH$_2$ (SEQ ID NO: 124); [Ura$^7$]hGLP-1(7-36)-NH$_2$ (SEQ ID NO: 125); [Paa$_7$]hGLP-1(7-36)-NH$_2$ (SEQ ID NO: 126); [Pta$^7$]hGLP-1(7-36)-NH$_2$ (SEQ ID NO: 127); [N-Me-Ala$^8$]hGLP-1(7-36)-NH$_2$ (SEQ ID NO: 128); [N-Me-Ala$^8$]hGLP-1(8-36)-NH$_2$; (SEQ ID NO. ) [N-Me-D-Ala$^8$]hGLP-1(7-36)-NH$_2$; [N-Me-D-Ala$^8$]hGLP-1(8-36)-NH$_2$; [N-Me-Gly$^8$]hGLP-1(7-36)-NH$_2$ (SEQ ID NO: 129); [A5c$^8$]hGLP-1(7-36)-NH$_2$ (SEQ ID NO: 130); [N-Me-Glu$^9$]hGLP-1(7-36)-NH$_2$ (SEQ ID NO: 131); [A5c$^8$, A6c$^{20,32}$]hGLP-1(7-36)-NH$_2$ (SEQ ID NO: 132); [Aib$^8$, A6c$^{32}$]hGLP-1(7-36)-NH$_2$ (SEQ ID NO: 133); [Aib$^{8,25}$]hGLP-1(7-36)-NH$_2$ (SEQ ID NO: 134); [Aib$^{8,24}$]hGLP-1(7-36)-NH$_2$ (SEQ ID NO: 135); [Aib$^{8,30}$]hGLP-1(7-36)-NH$_2$ (SEQ ID NO: 136); [Aib$^8$, Cha$^{20}$]hGLP-1(7-36)-NH$_2$ (SEQ ID NO: 137); [Aib$^8$, Cha$^{32}$]hGLP-1(7-36)-NH$_2$ (SEQ ID NO: 138); [Aib$^8$, Glu$^{23}$]hGLP-1(7-36)-NH$_2$ (SEQ ID NO: 139); [Aib$^8$, A6c$^{20}$]hGLP-1(7-36)-NH$_2$ (SEQ ID NO: 140); [Aib$^8$, A6c$^{20,32}$]hGLP-1(7-36)-NH$_2$ (SEQ ID NO: 141); [Aib$^{8,22}$]hGLP-1(7-36)-NH$_2$ (SEQ ID NO: 142); [Aib$^8$, β-Ala$^{22}$]hGLP-1(7-36)-NH$_2$ (SEQ ID NO: 143); [Aib$^8$, Lys$^{25}$]hGLP-1(7-36)-NH$_2$ (SEQ ID NO: 144); [Aib$^8$, A6c$^{12}$]hGLP-1(7-36)-NH$_2$ (SEQ ID NO: 145); [Aib$^8$, A6c$^{29}$]hGLP-1(7-36)-NH$_2$ (SEQ ID NO: 146); [Aib$^8$, A6c$^{33}$]hGLP-1(7-36)-NH$_2$ (SEQ ID NO: 147); [Aib$^{8,14}$]hGLP-1(7-36)-NH$_2$ (SEQ ID NO: 148); [Aib$^{8,18}$]hGLP-1(7-36)-NH$_2$ (SEQ ID NO: 149); or [Aib$^{8,17}$]hGLP-1(7-36)NH$_2$ (SEQ ID NO: 150); or a pharmaceutically acceptable salt thereof. In another aspect, the present invention provides a pharmaceutical composition comprising an effective amount of a compound of formula (I) as defined hereinabove or a pharmaceutically acceptable salt thereof and a pharmaceutically acceptable carrier or diluent.

In still another aspect, the present invention provides a method of eliciting an agonist effect from a GLP-1 receptor in a subject in need thereof which comprises administering to said subject an effective amount of a compound of formula (I) as defined hereinabove or a pharmaceutically acceptable salt thereof.

In yet a further aspect, this invention provides a method of treating a disease selected from the group consisting of Type I diabetes, Type II diabetes, obesity, glucagonomas, secretory disorders of the airway, metabolic disorder, arthritis, osteoporosis, central nervous system disease, restenosis and neurodegenerative disease, renal failure, congestive heart failure, nephrotic syndrome, cirrhosis, pulmonary edema, hypertension, and disorders wherein the reduction of food intake is desired, in a subject in need thereof which comprises administering to said subject an effective amount of a compound of formula (I) as defined hereinabove or a pharmaceutically acceptable salt thereof. Preferred of the foregoing method is where the disease is Type I diabetes or Type II diabetes.

With the exception of the N-terminal amino acid, all abbreviations (e.g. Ala) of amino acids in this disclosure stand for the structure of —NH—CH(R)—CO—, wherein R is the side chain of an amino acid (e.g., $CH_3$ for Ala). For the N-terminal amino acid, the abbreviation stands for the structure of $(R^2R^3)$—N—CH(R)—CO—, wherein R is a side chain of an amino acid and $R^2$ and $R^3$ are as defined above except in the case where $A^7$ is Ura, Paa, Pta or Hppa in which case $R^2$ and $R^3$ are not present since Ura, Paa, Pta and Hppa are considered here as des-amino amino acids. The abbreviations: β-Nal, Nle, Cha, Amp, 3-Pal, 4-Pal and Aib stand for the following α-amino acids; β-(2-naphthyl)alanine, norleucine, cyclohexylalanine, 4-amino-phenylalanine, β-(3-pyridinyl)alanine, β-(4-pyridinyl)alanine and α-aminoisobutyric acid, respectively. Other amino acid definitions are: Ura is urocanic acid; Pta is (4-pyridylthio)acetic acid; Pass is trans-3-(3-pyridyl)acrylic acid; Tma-His is N,N-tetramethylamidino-histidine; N-Me-Ala is N-methylalanine; N-Me-Gly is N-methyl-glycine; N-Me-Glu is N-methyl-glutamic acid; Tle is tert-butylglycine; Abu is α-aminobutyric acid; Tba is tert-butylalanine; Orn is ornithine; Aib is α-aminoisobutyric acid; β-Ala is β-alanine; Gaba is γ-aminobutyric acid; Ava is 5-aminovaleric acid; Aic is 2-aminoindane-2-carboxylic acid; and Hppa is 3-(ρ-hydroxyphenyl)propionic acid.

What is meant by Acc is an amino acid selected from the group of 1-amino-1-cyclopropanecarboxylic acid (A3c); 1-amino-1-cyclobutanecarboxylic acid (A4c); 1-amino-1-cyclopentanecarboxylic acid (A5c); 1-amino-1-cyclohexanecarboxylic acid (A6c); 1-amino-1-cycloheptanecarboxylic acid (A7c); 1-amino-1-cyclooctanecarboxylic acid (A8c); and 1-amino-1-cyclononanecarboxylic acid (A9c). In the above formula, hydroxyalkyl, hydroxyphenylalkyl, and hydroxynaphthylalkyl may contain 1-4 hydroxy substituents. $COX^5$ stands for $—C=O.X^5$. Examples of $—C=O.X^5$ include, but are not limited to, acetyl and phenylpropionyl.

What is means by Lys($N^ε$-alkanoyl) is represented by the following structure:

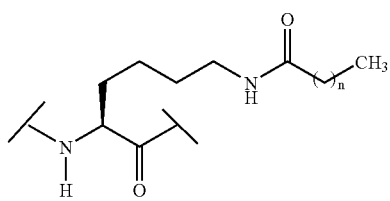

What is meant by Lys($N^ε$-alkylsulfonyl) is represented by the following structure:

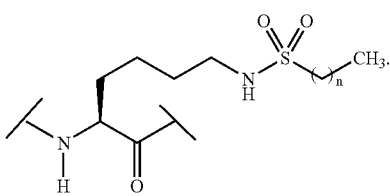

What is meant by Lys($N^ε$-(2-(4-alkyl-1-piperazine)-acetyl)) is represented by the following structure:

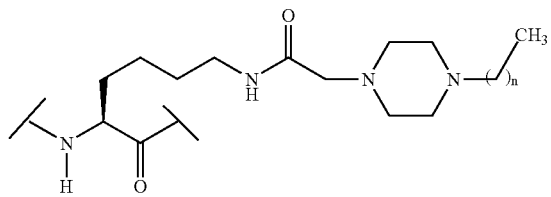

What is meant by Asp(1-(4-alkyl-piperazine)) is represented by the following structure:

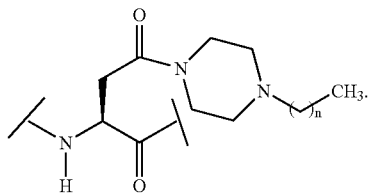

What is meant by Asp(1-alkylamino) is represented by the following structure:

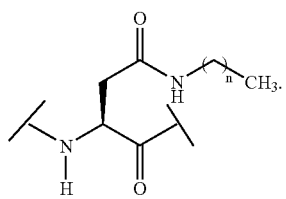

The variable n in the foregoing structures is 1 to 30.

The full names for other abbreviations used herein are as follows: Boc for t-butyloxycarbonyl, HF for hydrogen fluoride, Fm for formyl, Xan for xanthyl, Bzl for benzyl, Tos for tosyl, DNP for 2,4-dinitrophenyl, DMF for dimethylformamide, DCM for dichloromethane, HBTU for 2-(1H-Benzotriazol-1-yl)-1,1,3,3-tetramethyl uronium hexafluorophosphate, DIEA for diisopropylethylamine, HOAc for acetic acid, TFA for trifluoroacetic acid, 2CIZ for 2-chlorobenzyloxycarbonyl and OcHex for O-cyclohexyl.

A peptide of this invention is also denoted herein by another format, e.g., [A5c⁸]hGLP-1(7-36)-NH₂ (SEQ ID NO: 130), with the substituted amino acids from the natural sequence placed between the set of brackets (e.g., A5c⁸ for Ala⁸ in hGLP-1). The abbreviation GLP-1 means glucagon-like peptide-1, and hGLP-1 means human glucagon-like peptide-1. The numbers between the parentheses refer to the number of amino acids present in the peptide (e.g., hGLP-1(7-36) (SEQ ID NO: 3) is amino acids 7 through 36 of the peptide sequence for human GLP-1). The sequence for hGLP-1(7-37) (SEQ ID NO: 4) is listed in Mojsov, S., Int. J. Peptide Protein Res., 40, 1992, pp. 333-342. The designation "NH₂" in hGLP-1(7-36)NH₂ (SEQ ID NO: 1) indicates that the C-terminus of the peptide is amidated. hGLP-1(7-36) (SEQ ID NO: 2) means that the C-terminus is the free acid.

DETAILED DESCRIPTION

The peptides of this invention can be prepared by standard solid phase peptide synthesis. See, e.g., Stewart, J. M., et al., Solid Phase Synthesis (Pierce Chemical Co., 2d ed. 1984). The substituents $R^2$ and $R^3$ of the above generic formula can be attached to the free amine of the N-terminal amino acid by standard methods known in the art. For example, alkyl groups, e.g., $(C_1-C_{30})$alkyl, can be attached using reductive alkylation. Hydroxyalkyl groups, e.g., $(C_1-C_{30})$hydroxyalkyl, can also be attached using reductive alkylation wherein the free hydroxy group is protected with a t-butyl ester. Acyl groups, e.g., $COE^1$, may be attached by coupling the free acid, e.g., $E^1COOH$, to the free amine of the N-terminal amino acid by mixing the completed resin with 3 molar equivalents of both the free acid and diisopropylcarbodiimide in methylene chloride for one hour. If the free acid contains a free hydroxy group, e.g., p-hydroxyphenylpropionic acid, then the coupling should be performed with an additional 3 molar equivalents of HOBT.

When $R^1$ is $NH-X^2-CH_2-CONH_2$ (i.e., $Z^0=CONH_2$), the synthesis of the peptide starts with $BocNH-X^2-CH_2-COOH$ which is coupled to the MBHA resin. If $R^1$ is $NH-X^2-CH_2-COOH$ (i.e., $Z^0=COOH$) the synthesis of the peptide starts with $Boc-HN-X^2-CH_2-COOH$ which is coupled to PAM resin.

The following describes a synthetic method for making a peptide of this invention, which method is well-known to those skilled in the art. Other methods are also known to those skilled in the art.

Benzhydrylamine-polystyrene resin (Advanced ChemTech, Inc., Louisville, Ky.) (0.9 g, 0.3 mmole) in the chloride ion form is placed in a reaction vessel of an Advanced ChemTech Peptide Synthesizer Model 200 programmed to perform the following reaction cycle: (a) methylene chloride; (b) 33% trifluoroacetic acid in methylene chloride (2 times for 1 and 15 min each); (c) methylene chloride; (d) ethanol; (e) methylene chloride; (f) 10% diisopropylethylamine in methylene chloride.

The neutralized resin is stirred with Boc-protected amino acid which is to be the C-terminal amino acid of the desired peptide to be synthesized and diisopropylcarbodiimide (3 mmole each) in methylene chloride for 1 hour and the resulting amino acid resin is then cycled through steps (a) through (f) in the above wash program. The other amino acids (3 mmol) of the desired peptide are then coupled successively by the same procedure. The finished peptide is cleaved from the resin by mixing it with anisole (5 ml), dithiothreitol (100 mg) and anhydrous hydrogen fluoride (35 ml) at about 0° C. and stirring it for about 45 min. Excess hydrogen fluoride is evaporated rapidly under a stream of dry nitrogen and free peptide precipitated and washed with ether. The crude peptide is then dissolved in a minimum volume of dilute acetic acid and eluted on a column (2.5×25 cm) of VYDAC® octadecylsilane silica (10 mM) and eluted with a linear gradient of 20-60% acetonitrile over about 1 h in 0.1% trifluoroacetic acid in water. Fractions are examined by thin layer chromatography and analytical high performance liquid chromatography (40-70% B at 1%/min, solution B is 80% acetonitrile/water containing 0.1% TFA) and pooled to give maximum purity rather than yield. Repeated lyophilization of the solution from water gives the product as a white, fluffy powder.

The product peptide is analyzed by HPLC. Amino acid analysis of an acid hydrolysate of the product peptide can confirm the composition of the peptide. Laser desorption MS is used to determine the molecular weight of the peptide.

The protected amino acid 1-[N-tert-butoxycarbonylamino]-1-cyclohexane-carboxylic acid (Boc-A6c-OH) was synthesized as follows. 19.1 g (0.133 mol) of 1-amino-1-cyclohexanecarboxylic acid (Acros Organics, Fisher Scientific, Pittsburgh, Pa.) was dissolved in 200 ml of dioxane and 100 ml of water. To it was added 67 ml of 2N NaOH. The solution was cooled in an ice-water bath. 32.0 g (0.147 mol) of di-tert-butyl-dicarbonate was added to this solution. The reaction mixture was stirred overnight at room temperature. Dioxane was then removed under reduced pressure. 200 ml of ethyl acetate was added to the remaining aqueous solution. The mixture was cooled in an ice-water bath. The pH of the aqueous layer was adjusted to about 3 by adding 4N HCl. The organic layer was separated. The aqueous layer was extracted with ethyl acetate (1×100 ml). The two organic layers were combined and washed with water (2×150 ml), dried over anhydrous $MgSO_4$, filtered and concentrated to dryness under reduced pressure. The residue was recrystallized in ethyl acetate/hexanes. 9.2 g of the pure product was obtained. 29% yield.

Boc-A5c-OH was synthesized in an analogous manner to that of Boc-A6c-OH. Other protected Acc amino acids can be prepared in an analogous manner by a person of ordinary skill in the art as enabled by the teachings herein.

In the synthesis of a peptide of this invention containing A5c, A6c and/or Aib, the coupling time is about 2 hrs. for these residues and the residue immediately following them. For the synthesis of [Tma-His$^7$]hGLP-1(7-36)NH$_2$ (SEQ ID NO: 117), HBTU (2 mmol) and DIEA (1.0 ml) in 4 ml DMF were used to react with the N-terminal free amine of the peptide-resin in the last coupling reaction; the coupling time is about 2 hours.

The full names for the abbreviations used above are as follows: Boc for t-butyloxycarbonyl, HF for hydrogen fluoride, Fm for formyl, Xan for xanthyl, Bzl for benzyl, Tos for tosyl, DNP for 2,4-dinitrophenyl, DMF for dimethylformamide, DCM for dichloromethane, HBTU for 2-(1H-benzotriazol-1-yl)-1,1,3,3-tetramethyl uronium hexafluorophosphate, DIEA for diisopropylethylamine, HOAc for acetic acid, TFA for trifluoroacetic acid, 2CIZ for 2-chlorobenzyloxycarbonyl, 2BrZ for 2-bromobenzyloxycarbonyl and OcHex for O-cyclohexyl.

The substituents $R^2$ and $R^3$ of the above generic formula can be attached to the free amine of the N-terminal amino acid by standard methods known in the art. For example, alkyl groups, e.g., $(C_1-C_{30})$alkyl, may be attached using reductive alkylation. Hydroxyalkyl groups, e.g., $(C_1-C_{30})$ hydroxyalkyl, can also be attached using reductive alkylation wherein the free hydroxy group is protected with a t-butyl ester. Acyl groups, e.g., $COX^1$, can be attached by coupling the free acid, e.g., $X^1COOH$, to the free amine of the N-terminal amino acid by mixing the completed resin with 3 molar equivalents of both the free acid and diisopropylcarbodiimide in methylene chloride for about one hour. If the free acid contains a free hydroxy group, e.g., p-hydroxyphenylpropionic acid, then the coupling should be performed with an additional 3 molar equivalents of HOBT.

A compound of the present invention can be tested for activity as a GLP-1 binding compound according to the following procedure.

Cell Culture:

RIN 5F rat insulinoma cells (ATCC-# CRL-2058, American Type Culture Collection, Manassas, Va.), expressing the GLP-1 receptor, were cultured in Dulbecco's modified Eagle's medium (DMEM) containing 10% fetal calf serum, and maintained at about 37° C. in a humidified atmosphere of 5% $CO_2$/95% air.

Radioligand Binding:

Membranes were prepared for radioligand binding studies by homogenization of the RIN cells in 20 ml of ice-cold 50 mM Tris-HCl with a Brinkman Polytron (Westbury, N.Y.) (setting 6, 15 sec). The homogenates were washed twice by centrifugation (39,000 g/10 min), and the final pellets were re-suspended in 50 mM Tris-HCl, containing 2.5 mM $MgCl_2$, 0.1 mg/ml bacitracin (Sigma Chemical, St. Louis, Mo.), and 0.1% BSA. For assay, aliquots (0.4 ml) were incubated with 0.05 nM [$^{125}$I]GLP-1(7-36) (SEQ ID NO: 151(~2200 Ci/mmol, New England Nuclear, Boston, Mass.), with and without 0.05 ml of unlabeled competing test peptides. After a 100 min incubation (25° C.), the bound [$^{125}$I]GLP-1(7-36) (SEQ ID NO: 151) was separated from the free by rapid filtration through GF/C filters (Brandel, Gaithersburg, Md.), which had been previously soaked in 0.5% polyethyleneimine. The filters were then washed three times with 5 ml aliquots of ice-cold 50 mM Tris-HCl, and the bound radioactivity trapped on the filters was counted by gamma spectrometry (Wallac LKB, Gaithersburg, Md.). Specific binding was defined as the total [$^{125}$I]GLP-1(7-36) (SEQ ID NO: 151) bound minus that bound in the presence of 1000 nM GLP1(7-36) (SEQ ID NO: 3) (Bachem, Torrence, Calif.).

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids). A typical method of making a salt of a peptide of the present invention is well known in the art and can be accomplished by standard methods of salt exchange. Accordingly, the TFA salt of a peptide of the present invention (the TFA salt results from the purification of the peptide by using preparative HPLC, eluting with TFA containing buffer solutions) can be converted into another salt, such as an acetate salt by dissolving the peptide in a small amount of 0.25 N acetic acid aqueous solution. The resulting solution is applied to a semi-prep HPLC column (Zorbax, 300 SB, C-8). The column is eluted with (1) 0.1N ammonium acetate aqueous solution for 0.5 hrs., (2) 0.25N acetic acid aqueous solution 0.5 hrs. and (3) a linear gradient (20% to 100% of solution B over 30 min.) at a flow rate of 4 ml/min (solution A is 0.25N acetic acid aqueous solution; solution B is 0.25N acetic acid in acetonitrile/water, 80:20). The fractions containing the peptide are collected and lyophilized to dryness.

As is well known to those skilled in the art, the known and potential uses of GLP-1 is varied and multitudinous [See, Todd, J. F., et al., Clinical Science, 1998, 95, pp. 325-329; and Todd, J. F. et al., European Journal of Clinical Investigation, 1997, 27, pp. 533-536]. Thus, the administration of the compounds of this invention for purposes of eliciting an agonist effect can have the same effects and uses as GLP-1 itself. These varied uses of GLP-1 may be summarized as follows, treatment of: Type I diabetes, Type II diabetes, obesity, glucagonomas, secretory disorders of the airway, metabolic disorder, arthritis, osteoporosis, central nervous system diseases, restenosis and neurodegenerative diseases, GLP-1 analogues of the present invention that elicit an antagonist effect from a subject can be used for treating the following: hypoglycemia and malabsorption syndrome associated with gastroectomy or small bowel resection.

Accordingly, the present invention includes within its scope pharmaceutical compositions comprising, as an active ingredient, at least one of the compounds of formula (I) in association with a pharmaceutically acceptable carrier or diluent.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. In general, an effective dosage for the activities of this invention is in the range of $1 \times 10^{-7}$ to 200 mg/kg/day, preferably $1 \times 10^{-4}$ to 100 mg/kg/day, which can be administered as a single dose or divided into multiple doses.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents and patent applications. U.S. Pat. No.

5,672,659 teaches sustained release compositions comprising a bioactive agent and a polyester, U.S. Pat. No. 5,595,760 teaches sustained release compositions comprising a bioactive agent in a gelable form. U.S. application No. 08/929,363 filed Sep. 9, 1997, teaches polymeric sustained release compositions comprising a bioactive agent and chitosan. U.S. application No. 08/740,778 filed Nov. 1, 1996, teaches sustained release compositions comprising a bioactive agent and cyclodextrin. U.S. application No. 09/015,394 filed Jan. 29, 1998, teaches absorbable sustained release compositions of a bioactive agent. U.S. application No. 09/121,653 filed Jul. 23, 1998, teaches a process for making microparticles comprising a therapeutic agent such as a peptide in an oil-in-water process. U.S. application No. 09/131,472 filed Aug. 10, 1998, teaches complexes comprising a therapeutic agent such as a peptide and a phosphorylated polymer. U.S. application No. 09/184,413 filed Nov. 2, 1998, teaches complexes comprising a therapeutic agent such as a peptide and a polymer bearing a non-polymerizable lactone. The teachings of the foregoing patents and applications are incorporated herein by reference.

Unless defined otherwise, all technical and scientific terms used herein have the same meaning as commonly understood by one of ordinary skill in the art to which this invention belongs. Also, all publications, patent applications, patents and other references mentioned herein are incorporated by reference.

The following examples describe synthetic methods for making a peptide of this invention, which methods are well-known to those skilled in the art. Other methods are also known to those skilled in the art. The examples are provided for the purposes of illustration and is not meant to limit the scope of the present invention in any manner.

EXAMPLE 1

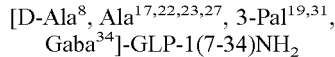

Benzhydrylamine-polystyrene resin (Advanced ChemTech, Inc. Louisville, Ky.) (0.9 g, 0.3 mmole) in the chloride ion form was placed in a reaction vessel of an Advanced ChemTech peptide synthesizer Model 200 programmed to perform the following reaction cycle: (a) methylene chloride; (b) 33% trifluoroacetic acid in methylene chloride (2 times for 1 and 15 min each); (c) methylene chloride; (d) ethanol; (e) methylene chloride; (f) 10% diisopropylethylamine in methylene chloride.

The neutralized resin was stirred with Boc-Gaba and diisopropylcarbodiimide (3 mmole each) in methylene chloride for 1 hour and the resulting amino acid resin was then cycled through steps (a) to (f) in the above wash program. The following amino acids (3 mmole) were then coupled successively by the same procedure: Boc-Val, Boc-Leu, Boc-3-Pal, Boc-Ala, Boc-Ile, Boc-Phe, Boc-Ala, Boc-Lys (2-Cl-Z), Boc-Ala, Boc-Ala, Boc-Ala, Boc-Ala, Boc-Glu (Bzl), Boc-Leu, Boc-3-Pal, Boc-Ser(Bzl), Boc-Ala, Boc-Val, Boc-Asp(Bzl), Boc-Ser(Bzl), Boc-Thr(Bzl), Boc-Phe, Boc-Thr(Bzl), Boc-Gly, Boc-Glu(Bzl), Boc-D-Ala, Boc-His (Bom).

The resin with the completed peptide sequence was mixed with anisole (5 ml), dithiothreitol (100 mg) and anhydrous hydrogen fluoride (35 ml) at about 0° C. and stirred for about 45 min. Excess hydrogen fluoride was evaporated rapidly under a stream of dry nitrogen and free peptide precipitated and washed with ether. The crude peptide was then dissolved in a minimum volume of dilute acetic acid and eluted on a column (2.5×25 cm) of VYDAC® octadecylsilane silica (10 mM) and eluted with a linear gradient of 20-60% acetonitrile over about 1 h in 0.1% trifluoroacetic acid in water. Fractions were examined by thin layer chromatography and analytical high performance liquid chromatography (40-70% B at 1%/min; r.t.: 14.1 min) and pooled to give maximum purity rather than yield. Repeated lyophilization of the solution from water gives the product (49.9 mg) as a white, fluffy powder.

The product was found to be homogeneous by HPLC and tlc. Amino acid analysis of an acid hydrolysate confirms the composition of the peptide. Laser desorption MS gave a MW of 2880 (Calc. M+H 2873).

EXAMPLE 2

Peptides are assembled on O-benzyl-polystyrene resin (often referred to as Merrifield resin) using the Boc amino acid protocol described in Example 1, except that Asp and Glu amino acid carboxyl side-chains are protected with an Fm (fluorenylmethyl ester) group. Completed peptide-resins are suspended in dilute DMF solutions of an appropriate lower alkylamine (such as ethylamine, propylamine, phenethylamine, 1,2-diaminoethane, etc.) and stirred at about 60° C. (for about 18 hrs) whereupon filtration, removal of solvents under reduced pressure and trituration of cleaved peptide oil with ether gives a solid, protected alkylamide peptide. This is then subjected to HF cleavage to remove additional side chain protecting groups and HPLC purification as described in Example 1.

EXAMPLES 3-5

Examples 3-5 can be synthesized substantially according to the procedure described in Example 1 using the appropriate protected amino acids to yield the noted peptides.

Example 3: [Aib$^8$, D-Ala$^{17}$, Ala$^{18,22,23,27}$, 3-Pal$^{19,31}$, Tle$^{16}$, Gaba$^{34}$]-GLP-1(7-34)NH$_2$ Example 4: [Aib$^8$, D-Ala$^{17}$, Ala$^{22,23,27}$, 3-Pal$^{19,31}$, Tle$^{16}$]-GLP-1(7-33)NH$_2$ Example 5: [Aib$^8$, D-Ala$^{17}$, Ala$^{22,23,27}$, 3-Pal$^{19,31}$, Tle$^{16,20}$]-GLP-1(7-33)NH$_2$

EXAMPLES 6-51

Examples 6-51 were made substantially according to the procedure described for Example 1 but using the appropriate protected amino acid to yield the noted peptide. MS were obtained by laser desorption MS (NA means not available).

Example 6: [D-Ala$^{8,23,27}$, 3-Pal$^{19,31}$]hGLP-1(7-35)-NH$_2$; MS=2971.0; Calc. MW=2974.4.

Example 7: [Ala$^{18,23,27}$, 3-Pal$^{19,31}$]hGLP-1(7-35)-NH$_2$ (SEQ ID NO: 83); MS=2954.4; Calc. MW=2958.4.

Example 8: [Ala$^{16,23,27}$, 3-Pal$^{19,31}$]hGLP-1(7-35)-NH$_2$ (SEQ ID NO: 84); MS=2943.0; Calc. MW=2946.3.

Example 9: [Ala$^{14,23,27}$, 3-Pal$^{19,31}$]hGLP-1(7-35)-NH$_2$ (SEQ ID NO: 85); MS=2956.0; Calc. MW=2958.4.

Example 10: [Ala$^{22,23,27}$, 3-Pal$^{19,31}$]hGLP-1(7-35)-NH$_2$ (SEQ ID NO: 86); MS=2981.0; Calc. MW=2988.4.

Example 11: [Hppa$^7$]hGLP-1(7-36)-NH$_2$ (SEQ ID NO: 87); MS=NA

Example 12: [Ala$^{15,23,27}$, 3-Pal$^{19,31}$]hGLP-1(7-35)-NH$_2$ (SEQ ID NO: 88); MS=2928.0; Calc. MW=2930.4.

Example 13: [Ala$^{17,23,27}$, 3-Pal$^{19,31}$]hGLP-1(7-35)-NH$_2$ (SEQ ID NO: 89); MS=2955.0; Calc. MW=2958.4.

Example 14: [Ala$^{22,23,27}$, 3-Pal$^{19,31}$, Gaba$^{34}$]hGLP-1(7-34)-NH$_2$ (SEQ ID NO: 90); MS=2896.0; Calc. MW=2888.3.

Example 15: [Ala$^{15,22,23,27}$, 3-Pal$^{19,31}$, Gaba$^{34}$]hGLP-1(7-34)-NH$_2$ (SEQ ID NO: 91); MS=2852.0; Calc. MW=2844.3.

Example 16: [Ala$^{17,22,23,27}$, 3-Pal$^{19,31}$, Gaba$^{34}$]hGLP-1(7-34)-NH$_2$ (SEQ ID NO: 92); MS=2880.0; Calc. MW=2872.3.

Example 17: [Ala$^{18,22,23,27}$, 3-Pal$^{19,31}$, Gaba$^{34}$]hGLP-1(7-34)-NH$_2$ (SEQ ID NO: 93); MS=2870.0; Calc. MW=2872.3.

Example 18: [Ala$^{21,22,23,27}$, 3-Pal$^{19,31}$, Gaba$^{34}$]hGLP-1(7-34)-NH$_2$ (SEQ ID NO: 94); MS=NA.

Example 19: [Ala$^{22,23,26,27}$, 3-Pal$^{19,31}$, Gaba$^{34}$]hGLP-1(7-34)-NH$_2$ (SEQ ID NO: 95); MS=2832.0; Calc. MW=2831.2.

Example 20: [Ala$^{22,23,27,32}$, 3-Pal$^{19,31}$, Gaba$^{34}$]hGLP-1(7-34)-NH$_2$ (SEQ ID NO: 96); MS=2855.0; Calc. MW=2846.2.

Example 21: [Ala$^{22,23,26,27}$, 3-Pal$^{19,31}$, Gaba$^{33}$]hGLP-1(7-33)-NH$_2$ (SEQ ID NO: 97); MS=2729.0; Calc. MW=2732.0.

Example 22: [Ala$^{22,23,27,31}$, 3-Pal$^{19,31}$, Gaba$^{33}$]hGLP-1(7-33)-NH$_2$ (SEQ ID NO: 98); MS=2711.6; Calc. MW=2712.0.

Example 23: [Ala$^{22,23,27,28}$, 3-Pal$^{19,31}$, Gaba$_{33}$]hGLP-1(7-33)-NH$_2$ (SEQ ID NO: 99); MS=2712.0; Calc. MW=2713.0.

Example 24: [Ala$^{22,23,27,29}$, 3-Pal$^{19,31}$, Gaba$^{33}$]hGLP-1(7-33)-NH$_2$ (SEQ ID NO: 100); MS=2746.9; Calc. MW=2747.1.

Example 25: [Ala$^{23,27}$, 3-Pal$^{19,31}$, Gaba$^{33}$]hGLP-1(7-33)-NH$_2$ (SEQ ID NO: 101); MS=2777.0; Calc. MW=2,775.1.

Example 26: [Ala$^{20,22,23,27}$, 3-Pal$^{19,31}$, Gaba$^{33}$]hGLP-1(7-33)-NH$_2$ (SEQ ID NO: 102); MS=2742.0; Calc. MW=2747.1.

Example 27: [Ala$^{22,23,27}$, 3-Pal$^{19,31}$, Gaba$^{33}$]hGLP-1(7-33)-NH$_2$ (SEQ ID NO: 103); MS=2786.7; Calc. MW=2789.1.

Example 28: [Ala$^{17,22,23,27}$, 3-Pal$^{19,31}$, Gaba$^{33}$]hGLP-1(7-33)-NH$_2$ (SEQ ID NO: 104); MS=2771.0; Calc. MW=2773.1.

Example 29: [D-Ala$^{10}$, Ala$^{22,23,27}$, 3-Pal$^{19,31}$, Gaba$^{33}$]hGLP-1(7-33)-NH$_2$; MS=2802.0; Calc. MW=2803.2.

Example 30: [D-Ala$^8$, Ala$^{17,23,27}$, 3-Pal$^{19,31}$]hGLP-1(7-34)-NH$_2$; MS=2905.0; Calc. MW=2901.3.

Example 31: [Ala$^{17,23,27}$, 3-Pal$^{19,26,31}$]hGLP-1(7-34)-NH$_2$ (SEQ ID NO: 105); MS=2920.0; Calc. MW=2921.3.

Example 32: [D-Ala$^8$, Ala$^{17}$, 3-Pal$^{19,31}$]hGLP-1(7-34)-NH$_2$; MS=2908.0 (Na$^+$ salt); Calc. MW=2885.3.

Example 33: [Ala$^{17,23,27}$, 3-Pal$^{19,31}$]hGLP-1(7-34)-NH$_2$ (SEQ ID NO: 106); MS=2907.0; Calc. MW=2901.3.

Example 34: [D-Ala$^8$, Ala$^{17,23,27}$, 3-Pal$^{19,31}$, Tle$^{29}$]hGLP-1(7-34)-NH$_2$; MS=2906.0; Calc. MW=2901.3.

Example 35: [D-Ala$^8$, Ala$^{17,23,27}$, 3-Pal$^{19,31}$, Tle$^{16}$]hGLP-1(7-34)-NH$_2$; MS=2914.0; Calc. MW=2915.4.

Example 36: [D-Ala$^8$, Ala$^{17,23,27}$, 3-Pal$^{19,31}$, Gaba$^{34}$]hGLP-1(7-34)-NH$_2$; MS=2856.8; Calc. MW=2858.2.

Example 37: [D-Ala$^{22}$, Ala$^{17,23,27}$, 3-Pal$^{19,31}$, Gaba$^{34}$]hGLP-1(7-34)-NH$_2$; MS=2871.0; Calc. MW=2872.3.

Example 38: [Aib$^8$, Ala$^{17,23,27}$, 3-Pal$^{19,31}$, Gaba$^{34}$]hGLP-1(7-34)-NH$_2$ (SEQ ID NO: 107); MS=2875.0; Calc. MW=2872.3.

Example 39: [D-Ala$^8$, Ala$^{17,22,23,27}$, 3-Pal$^{19,31}$]hGLP-1(7-33)-NH$_2$; MS=2786.0; Calc. MW=2787.2.

Example 40: [Aib$^8$, Ala$^{17,22,23,27}$, 3-Pal$^{19,31}$]hGLP-1(7-33)-NH$_2$ (SEQ ID NO: 108); MS=2800.0; Calc. MW=2801.2.

Example 41: [Ala$^{17,18,23,27}$, 3-Pal$^{19,31}$, Gaba$^{34}$]hGLP-1(7-34)-NH$_2$ (SEQ ID NO: 109); MS=2842.5; Calc. MW=2842.2.

Example 42: [Ala$^{17,23,27}$, 3-Pal$^{19,31}$, Gaba$^{34}$]hGLP-1(7-34)-NH$_2$ (SEQ ID NO: 110); MS=2871.0; Calc. MW=2872.3.

Example 43: [Tle$^{16}$, Ala$^{17,23,27}$, 3-Pal$^{19,31}$, Gaba$^{34}$]hGLP-1(7-34)-NH$_2$ (SEQ ID NO: 111); MS=2870.0; Calc. MW=2872.3.

Example 44: [N-Me-D-Ala$^8$, Ala$^{17,22,23,27}$, 3-Pal$^{19,31}$]hGLP-1(7-33)-NH$_2$; MS=2795.0; Calc. MW=2801.2.

Example 45: [Aib$^8$, Ala$^{17,18,22,23,27}$, 3-Pal$^9$]hGLP-1(7-33)-NH$_2$ (SEQ ID NO: 112); MS=2784.2; Calc. MW=2785.2.

Example 46: [Ala$^{17,18,22,23,27}$, 3-Pal$^{19,31}$, Tle$^{16,20}$, Gaba$^{34}$]hGLP-1(7-34)-NH$_2$ (SEQ ID NO: 113); MS=2871.9; Calc. MW=2870.3.

Example 47: [D-Ala$^8$, Ala$^{17,18,22,23,27}$, 3-Pal$^{19,31}$, Tle$^{18}$, Gaba$^{34}$]hGLP-1(7-34)-NH$_2$; MS=2870.0; Calc. MW=2870.3.

Example 48: [D-Ala$^{8,22}$, Ala$^{17,18,23,27}$, 3-Pal$^{19,31}$, Gaba$^{34}$]hGLP-1(7-34)-NH$_2$; MS=2856.3; Calc. MW=2856.3.

Example 49: [D-Ala$^{8,18}$, Ala$^{17,22,23,27}$, 3-Pal$^{19,31}$, Gaba$^{34}$]hGLP-1(7-34)-NH$_2$; MS=NA.

Example 50: [D-Ala$^{8,17}$, Ala$^{18,22,23,27}$, 3-Pal$^{19,31}$, Gaba$^{34}$]hGLP-1(7-34)-NH$_2$; MS=NA.

Example 51: [D-Ala$^8$, Ala$^{17,18,22,23,27}$, 3-Pal$^{19,31}$, Gaba$^{34}$]hGLP-1(7-34)-NH$_2$; MS=2861.6; Calc. MW=2856.3.

EXAMPLE 52

[Aib$^8$, A6c$^{32}$]hGLP-1(7-36)NH$_2$ (SEQ ID NO: 114)

The title peptide was synthesized on an Applied Biosystems (Foster City, Calif.) model 430A peptide synthesizer which was modified to do accelerated Boc-chemistry solid phase peptide synthesis. See Schnoizer, et al., Int. J. Peptide Protein Res., 40:180 (1992). 4-Methylbenzhydrylamine (MBHA) resin (Peninsula, Belmont, Calif.) with the substitution of 0.91 mmol/g was used. The Boc amino acids (Bachem, Calif., Torrance, Calif.; Nova Biochem., LaJolla, Calif.) were used with the following side chain protection: Boc-Ala-OH, Boc-Arg(Tos)-OH, Boc-Asp(OcHex)-OH, Boc-Tyr(2BrZ)-OH, Boc-His(DNP)-OH, Boc-Val-OH, Boc-Leu-OH, Boc-Gly-OH, Boc-Gln-OH, Boc-Ile-OH, Boc-Lys (2CIZ)-OH, Boc-Thr(Bzl)-OH, Boc-A6c-OH, Ser(Bzl)-OH, Boc-Phe-OH, Boc-Aib-OH, Boc-Glu(OcHex)-OH and Boc-Trp(Fm)-OH. The synthesis was carried out on a 0.20 mmol scale. The Boc groups were removed by treatment with 100% TFA for 2×1 min. Boc amino acids (2.5 mmol) were pre-activated with HBTU (2.0 mmol) and DIEA (1.0 ml) in 4 ml of DMF and were coupled without prior neutralization of the peptide-resin TFA salt. Coupling times were about 5 min except for the Boc-Aib-OH and Boc-A6c-OH residues and the following residues, Boc-Trp(Fm)-OH and Boc-His (DNP)-OH wherein the coupling times were about 2 hours.

At the end of the assembly of the peptide chain, the resin was treated with a solution of 20% mercaptoethanol/10% DIEA in DMF for 2×20 min to remove the DNP group on the His side chain. The N-terminal Boc group was then removed by treatment with 100% TFA for 2×2 min. After neutralization of the peptide-resin with 10% DIEA in DMF (1×1 min), the formyl group on the side of the chain of Trp was removed by treatment with a solution of 15% ethanolamine/15% water/70% DMF for 2×30 min. The partially-deprotected peptide-resin was washed with DMF and DCM and dried under reduced pressure. The final cleavage was done by stirring the peptide-resin in 10 ml of HF containing 1 ml of anisole and dithiothreitol (24 mg) at 0° C. for about 75 min.

HF was removed with a flow of nitrogen. The residue was washed with ether (6×10 ml) and extracted with 4N HOAc (6×10 ml).

The peptide mixture in the aqueous extract was purified on a reverse-phase preparative high pressure liquid chromatography (HPLC) using a reverse phase VYDAC® $C_{18}$ column (Nest Group, Southborough, Mass.). The column was eluted with a linear gradient (20% to 50% of solution B over 105 min) at a flow rate of 10 ml/min (Solution A=water containing 0.1% TFA; Solution B=acetonitrile containing 0.1% of TFA). Fractions were collected and checked on analytical HPLC. Those containing pure product were combined and lyophilized to dryness. 92 mg of a white solid was obtained. Purity was >99% based on analytical HPLC analysis. Electro-spray mass spectrometer analysis gave the molecular weight at 3324.2 (the calculated molecular weight is 3323.7).

The synthesis of other compounds of the present invention can be carried out in the same manner as described for the synthesis of [Aib$^8$, A6c$^{32}$]hGLP-1(7-36)NH$_2$ (SEQ ID NO: 114) in Example 52 above but using the appropriate protected amino acids depending on the desired peptide.

[(N$^\alpha$-HEPES-His)$^7$]hGLP-1(7-36)NH$_2$ (SEQ ID NO: 152) {HEPES is (4-(2-hydroxyethyl)-1-piperazine-ethanesulfonic acid)} can be synthesized as follows: After assembly of the peptide long chain on MBHA resin (0.20 mmol), the peptide-resin is treated with 100% TFA (2×2 min.) and washed with DMF and DCM. The resin is then neutralized with 10% DIEA in DMF for about 2 min. After washing with DMF and DCM, the resin is treated with 0.23 mmol of 2-chloro-1-ethanesulfonyl chloride and 0.7 mmol of DIEA in DMF for about 1 hour. The resin is washed with DMF and DCM and treated with 1.2 mmol of 2-hydroxyethylpiperazine for about 2 hours. The resin is washed with DMF and DCM and treated with different reagents ((1) 20% mercaptoethanol/10% DIEA in DMF and (2) 15% ethanolamine/15% water/70% DMF) to remove the DNP group from the His side chain and formyl group on the Trp side chain as described above before the final HF cleavage of the peptide from the resin.

[(N$^\alpha$-HEPA-His)$^7$]hGLP-1(7-36)NH$_2$ (SEQ ID NO:153) ([(4-(2-hydroxyethyl)-1-piperazineacetyl)-His$^7$]hGLP-1(7-36)NH$_2$) can be made substantially according to the procedure described immediately above for making [(N$^\alpha$-HEPES-His)$^7$]hGLP-1(7-36)NH$_2$ (SEQ ID NO: 152) except that 2-bromo-acetic anhydride is used in place of 2-chloro-1-ethanesulfonyl chloride.

EXAMPLES 53-90 AND 104

Examples 53-90 and 104 were made substantially according to Example 52 but using the appropriate protected amino acid.

Example 53: [A6c$^{20,32}$]hGLP-1(7-36)-NH$_2$ (SEQ ID NO:115); MS=3322.3; Calc. MW=3321.7.
Example 54: [Aib$^8$]hGLP-1(7-36)-NH$_2$ (SEQ ID NO:116); MS=3311.7; Calc. MW=3311.7.
Example 55: [(Tma-His)$^7$]hGLP-1(7-36)-NH$_2$ (SEQ ID NO:117); MS=3395.9; Calc. MW=3396.9.
Example 56: [A6c$^8$]hGLP-1(8-36)-NH$_2$ (SEQ ID NO:118); MS=3214.5; Calc. MW=3214.7.
Example 57: [A6c$^8$]hGLP-1(7-36)-NH$_2$ (SEQ ID NO:119); MS=3351.5; Calc. MW=3351.8.
Example 58: [A6c$^{16,20}$]hGLP-1(7-36)-NH$_2$ (SEQ ID NO:120); MS=3335.9; Calc. MW=3335.8.
Example 59: [A6c$^{29,32}$]hGLP-1(7-36)-NH$_2$ (SEQ ID NO:121); MS=3321.7; Calc. MW=3321.7.
Example 60: [A6c$^{20}$, Aib$^{24}$]hGLP-1(7-36)-NH$_2$ (SEQ ID NO:122); MS=3323.6; Calc. MW=3323.7.
Example 61: [Aib$^{24}$, A6c$^{29,32}$]hGLP-1(7-36)-NH$_2$ (SEQ ID NO:123); MS=3335.7; Calc. MW=3335.8.
Example 62: [A6c$^{16,29,32}$]hGLP-1(7-36)-NH$_2$ (SEQ ID NO:124); MS=3347.7; Calc. MW=3347.8.
Example 63: [Ura$^7$]hGLP-1(7-36)-NH$_2$ (SEQ ID NO:125); MS=3279.5; Calc. MW=3280.7.
Example 64: [Paa$^7$]hGLP-1(7-36)-NH$_2$ (SEQ ID NO:126); MS=3290.9; Calc. MW=3291.8.
Example 65: [Pta$^7$]hGLP-1(7-36)-NH$_2$ (SEQ ID NO:127); MS=3311.2; Calc. MW=3311.8.
Example 66: [N-Me-Ala$^8$]hGLP-1(7-36)-NH$_2$ (SEQ ID NO:128); MS=3311.4; Calc. MW=3311.7.
Example 67: [N-Me-D-Ala$^8$]hGLP-1(7-36)-NH$_2$; MS=3311.6; Calc. MW=3311.7.
Example 68: [N-Me-D-Ala$^8$]hGLP-1(8-36)-NH$_2$; MS=3174.0; Calc. MW=3174.6.
Example 69: [N-Me-Gly$^8$]hGLP-1(7-36)-NH$_2$ (SEQ ID NO:129); MS=3297.3; Calc. MW=3297.7.
Example 70: [A5c$^8$]hGLP-1(7-36)-NH$_2$ (SEQ ID NO:130); MS=3337.3; Calc. MW=3337.8.
Example 71: [N-Me-Glu$^9$]hGLP-1(7-36)-NH$_2$ (SEQ ID NO:131); MS=3311.4; Calc. MW=3311.7.
Example 72: [A5c$^8$, A6c$^{20,32}$]hGLP-1(7-36)-NH$_2$ (SEQ ID NO:132); MS=3361.4; Calc. MW=3361.8.
Example 73: [Aib$^8$, A6c$^{32}$]hGLP-1(7-36)-NH$_2$ (SEQ ID NO:133); MS=3323.2; Calc. MW=3323.7.
Example 74: [Aib$^{8,25}$]hGLP-1(7-36)-NH$_2$ (SEQ ID NO:134); MS=3325.8; Calc. MW=3325.7.
Example 75: [Aib$^{8,24}$]hGLP-1(7-36)-NH$_2$ (SEQ ID NO:135); MS=3325.8; Calc. MW=3325.7.
Example 76: [Aib$^{8,30}$]hGLP-1(7-36)-NH$_2$ (SEQ ID NO:136); MS=3326.1; Calc. MW=3325.7.
Example 77: [Aib$^8$, Cha$^{20}$]hGLP-1(7-36)-NH$_2$ (SEQ ID NO:137); MS=3351.8; Calc. MW=3351.8.
Example 78: [Aib$^8$, Cha$^{32}$]hGLP-1(7-36)-NH$_2$ (SEQ ID NO:138); MS=3352.0; Calc. MW=3351.8.
Example 79: [Aib$^8$, Glu$^{23}$]hGLP-1(7-36)-NH$_2$ (SEQ ID NO:139); MS=3311.7; Calc. MW=3312.7.
Example 80: [Aib$^8$, A6c$^{20}$]hGLP-1(7-36)-NH$_2$ (SEQ ID NO:140); MS=3323.6; Calc. MW=3323.7.
Example 81: [Aib$^8$, A6c$^{20,32}$]hGLP-1(7-36)-NH$_2$ (SEQ ID NO:141); MS=3335.3; Calc. MW=3335.7.
Example 82: [Aib$^{8,22}$]hGLP-1(7-36)-NH$_2$ (SEQ ID NO:142); MS=3339.8; Calc. MW=3339.8.
Example 83: [Aib$^8$, β-Ala$^{22}$]hGLP-1(7-36)-NH$_2$ (SEQ ID NO:143); MS=3325.6; Calc. MW=3325.8.
Example 84: [Aib$^8$, Lys$^{25}$]hGLP-1(7-36)-NH$_2$ (SEQ ID NO:144); MS=3369.0; Calc. MW=3368.8.
Example 85: [Aib$^8$, A6c$^{12}$]hGLP-1(7-36)-NH$_2$ (SEQ ID NO:145); MS=3289.8; Calc. MW=3289.7.
Example 86: [Aib$^8$, A6c$^{29}$]hGLP-1(7-36)-NH$_2$ (SEQ ID NO:146); MS=3323.9; Calc. MW=3323.7.
Example 87: [Aib$^8$, A6c$^{33}$]hGLP-1(7-36)-NH$_2$ (SEQ ID NO:147); MS=3338.0; Calc. MW=3337.8.
Example 88: [Aib$^{8,14}$]hGLP-1(7-36)-NH$_2$ (SEQ ID NO:148); MS=3309.8; Calc. MW=3309.7.
Example 89: [Aib$^{8,18}$]hGLP-1(7-36)-NH$_2$ (SEQ ID NO:149); MS=3309.7; Calc. MW=3309.7.
Example 90: [Aib$^{8,17}$]hGLP-1(7-36)-NH$_2$ (SEQ ID NO:150); MS=3309.4; Calc. MW=3309.7.
Example 104: [Aib$^8$, D-Arg;$^{26}$]hGLP-1(7-36)-NH$_2$; MS=3310.7; Calc. MW=3311.73.

EXAMPLE 91

[Aib$^8$, A5c$^{33}$]hGLP-1(7-36)NH$_2$ (SEQ ID NO: 154)

The title compound can be made substantially according to Example 52 using the appropriate protected amino acids.

EXAMPLE 92

[Aib$^8$, A6c$^{32}$, Lys36(N$^\epsilon$-tetradecanoyl)]hGLP-1(7-36)
NH$_2$ (SEQ ID NO: 155)

The Boc amino acids to be used are the same as those in the synthesis of [Aib$^8$, A6c$^{32}$]hGLP-1(7-36)NH$_2$ (SEQ ID NO: 114) (Example 52) except that Fmoc-Lys(Boc)-OH is used here for the Lys$^{38}$(N$^\epsilon$-tetradecanoyl) residue. The first amino acid residue is coupled to the resin manually on a shaker. 2.5 mmol of Fmoc-Lys(Boc)-OH is dissolved in 4 ml of 0.5N HBTU in DMF. To the solution is added 1 ml of DIEA. The mixture is shaken for about 2 min. To the solution is then added 0.2 mmol of MBHA resin (substitution=0.91 mmol/g). The mixture is shaken for about 1 hr. The resin is washed with DMF and treated with 100% TFA for 2×2 min to remove the Boc protecting group. The resin is washed with DMF. Myristic acid (2.5 mmol) is pre-activated with HBTU (2.0 mmol) and DIEA (1.0 ml) in 4 ml of DMF for 2 min and is coupled to the Fmoc-Lys-resin. The coupling time is about 1 hr. The resin is washed with DMF and treated with 25% piperidine in DMF for 2×20 min to remove the Fmoc protecting group. The resin is washed with DMF and transferred to the reaction vessel of the peptide synthesizer. The remainder of the synthesis and purification procedures of the peptide are the same as those in the synthesis of [Aib$^8$, A6c$^{32}$]hGLP-1(7-36)NH$_2$, (SEQ ID NO: 114)

The syntheses of other compounds containing Lys(N$^\epsilon$-alkanoyl) residue are carried out in an analogous manner as described for the synthesis of [Aib$^8$, A6c$^{32}$, Lys36(N$^\epsilon$-tetradecanoyl)]hGLP-1(7-36)NH$_2$ SEQ ID NO: 155). Fmoc-Lys(Boc)-OH amino acid is used for the residue of Lys(N$^\epsilon$-alkanoyl) in the peptide, while Boc-Lys(2ClZ)-OH amino acid is used for the residue of Lys. If the Lys(N$^\epsilon$-alkanoyl) residue is not at the C-terminus, the peptide fragment immediately prior to the Lys(N$^\epsilon$-alkanoyl) residue is assembled on the resin on the peptide synthesizer first.

EXAMPLES 93-98

Examples 93-98 can be made substantially according to the procedure described for Example 92 using the appropriate amino acids.

Example 93: [Aib$^8$, A6c$^{32}$, Lys$^{38}$(N$^\epsilon$-tetradecanoyl)]hGLP-1(7-36)NH$_2$ (SEQ ID NO: 155)
Example 94: [Aib$^8$, Arg$^{26,34}$, A6c$^{32}$, Lys$^{36}$(N$^\epsilon$-tetradecanoyl)]hGLP-1(7-36)NH$_2$ (SEQ ID NO: 156)
Example 95: [Aib$^8$, Arg$^{26}$, A6c$^{32}$, Lys$^{34}$(N$^\epsilon$-tetradecanoyl)] hGLP-1(7-36)NH$_2$ (SEQ ID NO: 157)
Example 96: [Aib$^8$, Lys$^{26}$(N$^\epsilon$-tetradecanoyl), A6c$^{32}$, Arg$^{34}$] hGLP-1(7-36)NH$_2$ (SEQ ID NO: 158)
Example 97: [Aib$^8$, Lys$^{36}$(N$^\epsilon$-octanoyl)]hGLP-1(7-36)NH$_2$ (SEQ ID NO: 159)
Example 98: [Aib$^8$, A6c$^{20,32}$, Lys$^{36}$(N$^\epsilon$-octanoyl)]hGLP-1 (7-36)NH$_2$ (SEQ ID NO: 160)

EXAMPLE 99

[Aib$^8$, Arg$^{26,34}$, A6c$^{32}$, Lys$^{36}$(N$^\epsilon$-tetradecanoyl)]
hGLP-1(7-36)-OH (SEQ ID NO: 161)

The Boc amino acids to be used are the same as those used in the synthesis of [Aib$^8$, A6c$^{32}$, Lys36(N$^\epsilon$-tetradecanoyl)] hGLP-1(7-36)NH$_2$ (SEQ ID NO: 162) (Example 92). Fmoc-Lys(Boc)-OH (2.5 mmol) is pre-activated with HBTU (2.0 mmol), HOBt (2.0 mmol) and DIEA (2.5 ml) in DMF (4 ml) for about 2 min. This amino acid is coupled to 235 mg of PAM resin (Chem-Impex, Wood Dale, Ill.; substitution=0.85 mmol/g) manually on a shaker. The coupling time is about 8 hrs. The remainder of the synthesis and purification procedures for making the peptide are the same as those described in Example 52.

The syntheses of other analogs of hGLP-1(7-36)-OH (SEQ ID NO: 3) and hGLP-1(7-37)-OH, (SEQ ID NO: 4) which contain Lys(N$^\epsilon$-alkanoyl) residue, are carried out in an analogous manner as described for the synthesis of [Aib$^8$, Arg$^{26,34}$, A6c$^{32}$, Lys$^{36}$(N$^\epsilon$-tetradecanoyl)]hGLP-1(7-36)-OH (SEQ ID NO: 161). Fmoc-Lys(Boc)-OH amino acid is used for the residue of Lys(N$^\epsilon$-alkanoyl) in the peptide, while Boc-Lys(2ClZ)-OH amino acid is used for the residue of Lys.

EXAMPLES 100-103

Examples 100-103 can be made substantially according to the procedure described for Example 99 using the appropriate amino acids.

Example 100: [Aib$^8$, Arg$^{26}$, A6c$^{32}$, Lys$^{34}$(N$^\epsilon$-tetradecanoyl)] hGLP-1(7-36)-OH (SEQ ID NO: 162)
Example 101: [Aib$^8$, Lys$^{26}$(N$^\epsilon$-tetradecanoyl), A6c$^{32}$, Arg$^{34}$] hGLP-1(7-36)-OH (SEQ ID NO: 163)
Example 102: [Aib$^8$, Arg$^{26,34}$, A6c$^{32}$, Lys$^{36}$(N$^\epsilon$-tetradecanoyl)]hGLP-1(7-37)-OH (SEQ ID NO: 164)
Example 103: [Aib$^8$, Arg$^{26}$, A6c$^{32}$, Lys$^{34}$(N$^\epsilon$-tetradecanoyl)] hGLP-1(7-37)-OH (SEQ ID NO: 165)

What is claimed is:

1. A compound wherein said compound is
[D-Ala$^8$, Ala$^{17,22,23,27}$, 3-Pal$^{19,31}$, Gaba$^{34}$]-GLP-1(7-34)NH$_2$;
[D-Ala$^{8,23,27}$, 3-Pal$^{19,31}$]hGLP-1(7-35)-NH$_2$;
[Ala$^{18,23,27}$, 3-Pal$^{19,31}$]hGLP-1(7-35)-NH$_2$ (SEQ ID NO: 83);
[Ala$^{16,23,27}$, 3-Pal$^{19,31}$]hGLP-1(7-35)-NH$_2$ (SEQ ID NO: 84);
[Ala$^{14,23,27}$, 3-Pal$^{19,31}$]hGLP-1(7-35)-NH$_2$ (SEQ ID NO: 85);
[Ala$^{22,23,27}$, 3-Pal$^{19,31}$]hGLP-1(7-35)-NH$_2$ (SEQ ID NO: 86);
[Hppa$^7$]hGLP-1(7-36)-NH$_2$ (SEQ ID NO: 87);
[Ala$^{15,23,27}$, 3-Pal$^{19,31}$]hGLP-1(7-35)-NH$_2$ (SEQ ID NO: 88);
[Ala$^{17,23,27}$, 3-Pal$^{19,31}$]hGLP-1(7-35)-NH$_2$ (SEQ ID NO: 89);
[Ala$^{22,23,27}$, 3-Pal$^{19,31}$, Gaba$^{34}$]hGLP-1(7-34)-NH$_2$ (SEQ ID NO: 90);
[Ala$^{15,22,23,27}$, 3-Pal$^{19,31}$, Gaba$^{34}$]hGLP-1(7-34)-NH$_2$ (SEQ ID NO: 91);
[Ala$^{17,22,23,27}$, 3-Pal$^{19,31}$, Gaba$^{34}$]hGLP-1(7-34)-NH$_2$ (SEQ ID NO: 92);
[Ala$^{18,22,23,27}$, 3-Pal$^{19,31}$, Gaba$^{34}$]hGLP-1(7-34)-NH$_2$ (SEQ ID NO: 93);
[Ala$^{21,22,23,27}$, 3-Pal$^{19,31}$, Gaba$^{34}$]hGLP-1(7-34)-NH$_2$ (SEQ ID NO: 94);
[Ala$^{22,23,26,27}$, 3-Pal$^{19,31}$, Gaba$^{34}$]hGLP-1(7-34)-NH$_2$ (SEQ ID NO: 95);
[Ala$^{22,23,27,32}$, 3-Pal$^{19,31}$, Gaba$^{34}$]hGLP-1(7-34)-NH$_2$ (SEQ ID NO: 96);
[Ala$^{22,23,26,27}$, 3-Pal$^{19,31}$, Gaba$^{33}$]hGLP-1(7-33)-NH$_2$ (SEQ ID NO: 97);
[Ala$^{22,23,27,31}$, 3-Pal$^{19}$, Gaba$^{33}$]hGLP-1(7-33)-NH$_2$ (SEQ ID NO: 98);
[Ala$^{22,23,27,28}$, 3-Pal$^{19,31}$, Gaba$^{33}$]hGLP-1(7-33)-NH$_2$ (SEQ ID NO: 99);
[Ala$^{22,23,27,29}$, 3-Pal$^{19,31}$, Gaba$^{33}$]hGLP-1(7-33)-NH$_2$ (SEQ ID NO: 100);
[Ala$^{23,27}$, 3-Pal$^{19,31}$, Gaba$^{33}$]hGLP-1(7-33)-NH$_2$ (SEQ ID NO: 101);
[Ala$^{20,22,23,27}$, 3-Pal$^{19,31}$, Gaba$^{33}$]hGLP-1(7-33)-NH$_2$ (SEQ ID NO: 102);
[Ala$^{22,23,27}$, 3-Pal$^{19,31}$, Gaba$^{33}$]hGLP-1(7-33)-NH$_2$ (SEQ ID NO: 103);
[Ala$^{17,22,23,27}$, 3-Pal$^{19,31}$, Gaba$^{33}$]hGLP-1(7-33)-NH$_2$ (SEQ ID NO: 104);
[D-Ala$^{10}$, Ala$^{22,23,27}$, 3-Pal$^{19,31}$, Gaba$^{33}$]hGLP-1(7-33)-NH$_2$;
[D-Ala$^8$, Ala$^{17,23,27}$, 3-Pal$^{19,31}$]hGLP-1(7-34)-NH$_2$;
[Ala$^{17,23,27}$, 3-Pal$^{19,26,31}$]hGLP-1(7-34)-NH$_2$ (SEQ ID NO: 105);
[D-Ala$^8$, Ala$^{17}$, 3-Pal$^{19,31}$]hGLP-1(7-34)-NH$_2$;
[Ala$^{17,23,27}$, 3-Pal$^{19,31}$]hGLP-1(7-34)-NH$_2$ (SEQ ID NO: 106);
[D-Ala$^8$, Ala$^{17,23,27}$, 3-Pal$^{19,31}$, Tle$^{29}$]hGLP-1(7-34)-NH$_2$;
[D-Ala$^8$, Ala$^{17,23,27}$, 3-Pal$^{19,31}$, Tle$^{16}$]hGLP-1(7-34)-NH$_2$;
[D-Ala$^8$, Ala$^{17,23,27}$, 3-Pal$^{19,31}$, Gaba$^{34}$]hGLP-1(7-34)-NH$_2$;
[D-Ala$^{22}$, Ala$^{17,23,27}$, 3-Pal$^{19,31}$, Gaba$^{34}$]hGLP-1(7-34)-NH$_2$;
[Aib$^8$, Ala$^{17,23,27}$, 3-Pal$^{19,31}$, Gaba$^{34}$]hGLP-1(7-34)-NH$_2$ (SEQ ID NO: 107);
[D-Ala$^8$, Ala$^{17,22,23,27}$, 3-Pal$^{19,31}$]hGLP-1(7-33)-NH$_2$;
[Aib$^8$, Ala$^{17,22,23,27}$, 3-Pal$^{19,31}$]hGLP-1(7-33)-NH$_2$ (SEQ ID NO: 108);
[Ala$^{17,18,23,27}$, 3-Pal$^{19,31}$, Gaba$^{34}$]hGLP-1(7-34)-NH$_2$ (SEQ ID NO: 109);
[Ala$^{17,23,27}$, 3-Pal$^{19,31}$, Tle$^{33}$, Gaba$^{34}$]hGLP-1(7-34)-NH$_2$ (SEQ ID NO: 110);
[Tle$^{16}$, Ala$^{17,23,27}$, 3-Pal$^{19,31}$, Gaba$^{34}$]hGLP-1(7-34)-NH$_2$ (SEQ ID NO: 111);
[N-Me-D-Ala$^8$, Ala$^{17,22,23,27}$, 3-Pal$^{19,31}$]hGLP-1(7-33)-NH$_2$;
[Aib$^8$, Ala$^{17,18,22,23,27}$, 3-Pal$^{19,31}$]hGLP-1(7-33)-NH$_2$ (SEQ ID NO: 112);
[Ala$^{17,18,22,23,27}$, 3-Pal$^{19,31}$, Tle$^{16,20}$, Gaba$^{34}$]hGLP-1(7-34)-NH$_2$ (SEQ ID NO: 113);
[D-Ala$^8$, Ala$^{17,18,22,23,27}$, 3-Pal$^{19,31}$, Tle$^{16}$, Gaba$^{34}$]hGLP-1(7-34)-NH$_2$;
[D-Ala$^{8,22}$, Ala$^{17,18,23,27}$, 3-Pal$^{19,31}$, Gaba$^{34}$]hGLP-1(7-34)-NH$_2$;
[D-Ala$^{8,18}$, Ala$^{17,22,23,27}$, 3-Pal$^{19,31}$, Gaba$^{34}$]hGLP-1(7-34)-NH$_2$;
[D-Ala$^{8,17}$, Ala$^{18,22,23,27}$, 3-Pal$^{19,31}$, Gaba$^{34}$]hGLP-1(7-34)-NH$_2$; or
[D-Ala$^8$, Ala$^{17,18,22,23,27}$, 3-Pal$^{19,31}$, Gaba$^{34}$]hGLP-1(7-34)-NH$_2$; or a pharmaceutically acceptable salt thereof.

2. A method of eliciting an agonist effect from a GLP-1 receptor in a subject in need thereof comprising administering to said subject an effective amount of a compound according to claim 1 or a pharmaceutically acceptable salt thereof.

3. A method of treating Type II diabetes, in a subject in need thereof which comprises administering to said subject an effective amount of a compound according to claim 1 or a pharmaceutically acceptable salt thereof.

* * * * *

SEQUENCE LISTING

<160> NUMBER OF SEQ ID NOS: 165

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 1

His Ala Glu Gly Thr Phe Thr Ser Asp Val Ser Ser Tyr Leu Glu Gly
 1               5                   10                  15

```
Gln Ala Ala Lys Glu Phe Ile Ala Trp Leu Val Lys Gly Arg
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 2

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 3
<211> LENGTH: 30
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 4
<211> LENGTH: 31
<212> TYPE: PRT
<213> ORGANISM: Homo sapiens

<400> SEQUENCE: 4

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (20)
<223> OTHER INFORMATION: N-epsilon-alkanoyl-lysine

<400> SEQUENCE: 5

His Ala Glu Gly Thr Phe Thr Ser Asp Val Ser Ser Tyr Leu Glu Gly
 1               5                  10                  15

Gln Ala Ala Xaa Glu Phe Ile Ala Trp Leu Val Lys Gly Arg
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (20)
```

-continued

```
<223> OTHER INFORMATION: N-epsilon-alkanoyl-lysine

<400> SEQUENCE: 6

His Ala Glu Gly Thr Phe Thr Ser Asp Val Ser Ser Tyr Leu Glu Gly
 1               5                  10                  15

Gln Ala Ala Xaa Glu Phe Ile Ala Trp Leu Val Lys Gly Arg Gly
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (20)
<223> OTHER INFORMATION: N-epsilon-alkanoyl-lysine
<220> FEATURE:
<223> OTHER INFORMATION: this sequence has an amidated c-terminus

<400> SEQUENCE: 7

His Ala Glu Gly Thr Phe Thr Ser Asp Val Ser Ser Tyr Leu Glu Gly
 1               5                  10                  15

Gln Ala Ala Xaa Glu Phe Ile Ala Trp Leu Val Lys Gly Arg
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (20)
<223> OTHER INFORMATION: N-epsilon-alkanoyl-lysine
<220> FEATURE:
<223> OTHER INFORMATION: this sequence has an amidated c-terminus

<400> SEQUENCE: 8

His Ala Glu Gly Thr Phe Thr Ser Asp Val Ser Ser Tyr Leu Glu Gly
 1               5                  10                  15

Gln Ala Ala Xaa Glu Phe Ile Ala Trp Leu Val Lys Gly Arg Gly
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (28)
<223> OTHER INFORMATION: N-epsilon-alkanoyl-lysine

<400> SEQUENCE: 9

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Xaa Gly Arg
            20                  25                  30

<210> SEQ ID NO 10
<211> LENGTH: 31
<212> TYPE: PRT
<213> ORGANISM: Artificial Sequence
```

```
<220> FEATURE:
<223> OTHER INFORMATION: Description of Artificial Sequence: Mutagen
<220> FEATURE:
<221> NAME/KEY: MOD_RES
<222> LOCATION: (28)
<223> OTHER INFORMATION: N-epsilon-alkanoyl-lysine

<400> SEQUENCE: 10

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Xaa Gly Arg Gly
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (28)
<223> OTHER INFORMATION: N-epsilon-alkanoyl-lysine
<220> FEATURE:
<223> OTHER INFORMATION: this sequence has an amidated c-terminus

<400> SEQUENCE: 11

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Xaa Gly Arg
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (28)
<223> OTHER INFORMATION: N-epsilon-alkanoyl-lysine
<220> FEATURE:
<223> OTHER INFORMATION: this sequence has an amidated c-terminus

<400> SEQUENCE: 12

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Xaa Gly Arg Gly
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (20)
<223> OTHER INFORMATION: N-epsilon-alkanoyl-lysine
<220> FEATURE:
<221> NAME/KEY: MOD_RES
<222> LOCATION: (28)
<223> OTHER INFORMATION: N-epsilon-alkanoyl-lysine

<400> SEQUENCE: 13

His Ala Glu Gly Thr Phe Thr Ser Asp Val Ser Ser Tyr Leu Glu Gly
 1               5                  10                  15
```

```
Gln Ala Ala Xaa Glu Phe Ile Ala Trp Leu Val Xaa Gly Arg
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (20)
<223> OTHER INFORMATION: N-epsilon-alkanoyl-lysine
<220> FEATURE:
<221> NAME/KEY: MOD_RES
<222> LOCATION: (28)
<223> OTHER INFORMATION: N-epsilon-alkanoyl-lysine

<400> SEQUENCE: 14

His Ala Glu Gly Thr Phe Thr Ser Asp Val Ser Ser Tyr Leu Glu Gly
  1               5                  10                  15

Gln Ala Ala Xaa Glu Phe Ile Ala Trp Leu Val Xaa Gly Arg Gly
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (20)
<223> OTHER INFORMATION: N-epsilon-alkanoyl-lysine
<220> FEATURE:
<221> NAME/KEY: MOD_RES
<222> LOCATION: (28)
<223> OTHER INFORMATION: N-epsilon-alkanoyl-lysine
<220> FEATURE:
<223> OTHER INFORMATION: this sequence has an amidated c-terminus

<400> SEQUENCE: 15

His Ala Glu Gly Thr Phe Thr Ser Asp Val Ser Ser Tyr Leu Glu Gly
  1               5                  10                  15

Gln Ala Ala Xaa Glu Phe Ile Ala Trp Leu Val Xaa Gly Arg
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (20)
<223> OTHER INFORMATION: N-epsilon-alkanoyl-lysine
<220> FEATURE:
<221> NAME/KEY: MOD_RES
<222> LOCATION: (28)
<223> OTHER INFORMATION: N-epsilon-alkanoyl-lysine
<220> FEATURE:
<223> OTHER INFORMATION: this sequence has an amidated c-terminus

<400> SEQUENCE: 16

His Ala Glu Gly Thr Phe Thr Ser Asp Val Ser Ser Tyr Leu Glu Gly
  1               5                  10                  15

Gln Ala Ala Xaa Glu Phe Ile Ala Trp Leu Val Xaa Gly Arg Gly
            20                  25                  30
```

<210> SEQ ID NO 17
<211> LENGTH: 29
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (27)
<223> OTHER INFORMATION: N-epsilon-alkanoyl-lysine

<400> SEQUENCE: 17

Ala Glu Gly Thr Phe Thr Ser Asp Val Ser Ser Tyr Leu Glu Gly Gln
 1               5                  10                  15

Ala Ala Arg Glu Phe Ile Ala Trp Leu Val Xaa Gly Arg
            20                  25

<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (27)
<223> OTHER INFORMATION: N-epsilon-alkanoyl-lysine

<400> SEQUENCE: 18

Ala Glu Gly Thr Phe Thr Ser Asp Val Ser Ser Tyr Leu Glu Gly Gln
 1               5                  10                  15

Ala Ala Arg Glu Phe Ile Ala Trp Leu Val Xaa Gly Arg Gly
            20                  25                  30

<210> SEQ ID NO 19
<211> LENGTH: 29
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (27)
<223> OTHER INFORMATION: N-epsilon-alkanoyl-lysine
<220> FEATURE:
<223> OTHER INFORMATION: this sequence has an amidated c-terminus

<400> SEQUENCE: 19

Ala Glu Gly Thr Phe Thr Ser Asp Val Ser Ser Tyr Leu Glu Gly Gln
 1               5                  10                  15

Ala Ala Arg Glu Phe Ile Ala Trp Leu Val Xaa Gly Arg
            20                  25

<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (27)
<223> OTHER INFORMATION: N-epsilon-alkanoyl-lysine
<220> FEATURE:
<223> OTHER INFORMATION: this sequence has an amidated c-terminus

<400> SEQUENCE: 20

Ala Glu Gly Thr Phe Thr Ser Asp Val Ser Ser Tyr Leu Glu Gly Gln
1               5                   10                  15

Ala Ala Arg Glu Phe Ile Ala Trp Leu Val Xaa Gly Arg Gly
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (30)
<223> OTHER INFORMATION: N-epsilon-alkanoyl-lysine

<400> SEQUENCE: 21

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Xaa
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (30)
<223> OTHER INFORMATION: N-epsilon-alkanoyl-lysine

<400> SEQUENCE: 22

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Xaa Gly
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (30)
<223> OTHER INFORMATION: N-epsilon-alkanoyl-lysine
<220> FEATURE:
<223> OTHER INFORMATION: this sequence has an amidated c-terminus

<400> SEQUENCE: 23

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Xaa
            20                  25                  30

<210> SEQ ID NO 24
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (30)
<223> OTHER INFORMATION: N-epsilon-alkanoyl-lysine
<220> FEATURE:
<223> OTHER INFORMATION: this sequence has an amidated c-terminus

<400> SEQUENCE: 24

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Xaa Gly
            20                  25                  30

<210> SEQ ID NO 25
<211> LENGTH: 30
<212> TYPE: PRT
<213> ORGANISM: Homo sapiens

<400> SEQUENCE: 25

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Arg
            20                  25                  30

<210> SEQ ID NO 26
<211> LENGTH: 31
<212> TYPE: PRT
<213> ORGANISM: Homo sapiens

<400> SEQUENCE: 26

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Arg Gly
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 27

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Arg
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 28

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Lys Gly Arg Gly
            20                  25                  30

<210> SEQ ID NO 29
<211> LENGTH: 30
<212> TYPE: PRT

```
<213> ORGANISM: Homo sapiens

<400> SEQUENCE: 29

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Arg Gly Arg
            20                  25                  30

<210> SEQ ID NO 30
<211> LENGTH: 31
<212> TYPE: PRT
<213> ORGANISM: Homo sapiens

<400> SEQUENCE: 30

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Arg Gly Arg Gly
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 31

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Arg Gly Arg
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 32

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Arg Gly Arg Gly
            20                  25                  30

<210> SEQ ID NO 33
<211> LENGTH: 30
<212> TYPE: PRT
<213> ORGANISM: Homo sapiens

<400> SEQUENCE: 33

His Ala Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Gly Arg
            20                  25                  30

<210> SEQ ID NO 34
<211> LENGTH: 31
<212> TYPE: PRT
<213> ORGANISM: Homo sapiens
```

<400> SEQUENCE: 34

His Ala Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Gly Arg Gly
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 35

His Ala Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Gly Arg
            20                  25                  30

<210> SEQ ID NO 36
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 36

His Ala Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Gly Arg Gly
            20                  25                  30

<210> SEQ ID NO 37
<211> LENGTH: 30
<212> TYPE: PRT
<213> ORGANISM: Homo sapiens

<400> SEQUENCE: 37

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Lys
            20                  25                  30

<210> SEQ ID NO 38
<211> LENGTH: 31
<212> TYPE: PRT
<213> ORGANISM: Homo sapiens

<400> SEQUENCE: 38

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Lys Gly
            20                  25                  30

<210> SEQ ID NO 39
<211> LENGTH: 30
<212> TYPE: PRT
<213> ORGANISM: Artificial Sequence
<220> FEATURE:

-continued

```
<223> OTHER INFORMATION: Description of Artificial Sequence: Mutagen
<220> FEATURE:
<223> OTHER INFORMATION: this sequence has an amidated c-terminus

<400> SEQUENCE: 39

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Lys
            20                  25                  30

<210> SEQ ID NO 40
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 40

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Lys Gly
            20                  25                  30

<210> SEQ ID NO 41
<211> LENGTH: 30
<212> TYPE: PRT
<213> ORGANISM: Homo sapiens

<400> SEQUENCE: 41

His Ala Glu Gly Thr Phe Thr Ser Asp Val Ser Ser Tyr Leu Glu Gly
 1               5                  10                  15

Gln Ala Ala Arg Glu Phe Ile Ala Trp Leu Val Lys Gly Lys
            20                  25                  30

<210> SEQ ID NO 42
<211> LENGTH: 31
<212> TYPE: PRT
<213> ORGANISM: Homo sapiens

<400> SEQUENCE: 42

His Ala Glu Gly Thr Phe Thr Ser Asp Val Ser Ser Tyr Leu Glu Gly
 1               5                  10                  15

Gln Ala Ala Arg Glu Phe Ile Ala Trp Leu Val Lys Gly Lys Gly
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 43

His Ala Glu Gly Thr Phe Thr Ser Asp Val Ser Ser Tyr Leu Glu Gly
 1               5                  10                  15

Gln Ala Ala Arg Glu Phe Ile Ala Trp Leu Val Lys Gly Lys
            20                  25                  30

<210> SEQ ID NO 44
<211> LENGTH: 31
```

```
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 44

His Ala Glu Gly Thr Phe Thr Ser Asp Val Ser Ser Tyr Leu Glu Gly
  1               5                  10                  15

Gln Ala Ala Arg Glu Phe Ile Ala Trp Leu Val Lys Gly Lys Gly
             20                  25                  30

<210> SEQ ID NO 45
<211> LENGTH: 30
<212> TYPE: PRT
<213> ORGANISM: Homo sapiens

<400> SEQUENCE: 45

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Arg Gly Lys
             20                  25                  30

<210> SEQ ID NO 46
<211> LENGTH: 31
<212> TYPE: PRT
<213> ORGANISM: Homo sapiens

<400> SEQUENCE: 46

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Arg Gly Lys Gly
             20                  25                  30

<210> SEQ ID NO 47
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 47

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Arg Gly Lys
             20                  25                  30

<210> SEQ ID NO 48
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 48

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Arg Gly Lys Gly
             20                  25                  30
```

```
<210> SEQ ID NO 49
<211> LENGTH: 30
<212> TYPE: PRT
<213> ORGANISM: Homo sapiens

<400> SEQUENCE: 49

His Ala Glu Gly Thr Phe Thr Ser Asp Val Ser Ser Tyr Leu Glu Gly
  1               5                  10                  15

Gln Ala Ala Arg Glu Phe Ile Ala Trp Leu Val Arg Gly Lys
             20                  25                  30

<210> SEQ ID NO 50
<211> LENGTH: 31
<212> TYPE: PRT
<213> ORGANISM: Homo sapiens

<400> SEQUENCE: 50

His Ala Glu Gly Thr Phe Thr Ser Asp Val Ser Ser Tyr Leu Glu Gly
  1               5                  10                  15

Gln Ala Ala Arg Glu Phe Ile Ala Trp Leu Val Arg Gly Lys Gly
             20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 51

His Ala Glu Gly Thr Phe Thr Ser Asp Val Ser Ser Tyr Leu Glu Gly
  1               5                  10                  15

Gln Ala Ala Arg Glu Phe Ile Ala Trp Leu Val Arg Gly Lys
             20                  25                  30

<210> SEQ ID NO 52
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 52

His Ala Glu Gly Thr Phe Thr Ser Asp Val Ser Ser Tyr Leu Glu Gly
  1               5                  10                  15

Gln Ala Ala Arg Glu Phe Ile Ala Trp Leu Val Arg Gly Lys Gly
             20                  25                  30

<210> SEQ ID NO 53
<211> LENGTH: 30
<212> TYPE: PRT
<213> ORGANISM: Homo sapiens

<400> SEQUENCE: 53

His Ala Glu Gly Thr Phe Thr Ser Asp Val Ser Ser Tyr Leu Asp Gly
  1               5                  10                  15

Gln Ala Ala Lys Glu Phe Ile Ala Trp Leu Val Lys Gly Arg
             20                  25                  30
```

<210> SEQ ID NO 54
<211> LENGTH: 31
<212> TYPE: PRT
<213> ORGANISM: Homo sapiens

<400> SEQUENCE: 54

His Ala Glu Gly Thr Phe Thr Ser Asp Val Ser Ser Tyr Leu Asp Gly
 1               5                  10                  15

Gln Ala Ala Lys Glu Phe Ile Ala Trp Leu Val Lys Gly Arg Gly
            20                  25                  30

<210> SEQ ID NO 55
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 55

His Ala Glu Gly Thr Phe Thr Ser Asp Val Ser Ser Tyr Leu Asp Gly
 1               5                  10                  15

Gln Ala Ala Lys Glu Phe Ile Ala Trp Leu Val Lys Gly Arg
            20                  25                  30

<210> SEQ ID NO 56
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 56

His Ala Glu Gly Thr Phe Thr Ser Asp Val Ser Ser Tyr Leu Asp Gly
 1               5                  10                  15

Gln Ala Ala Lys Glu Phe Ile Ala Trp Leu Val Lys Gly Arg Gly
            20                  25                  30

<210> SEQ ID NO 57
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid

<400> SEQUENCE: 57

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 58
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)

```
<223> OTHER INFORMATION: alpha-aminoisobutyric acid

<400> SEQUENCE: 58

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 59
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<223> OTHER INFORMATION: this sequence has an amidated c-terminus

<400> SEQUENCE: 59

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 60
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<223> OTHER INFORMATION: this sequence has an amidated c-terminus

<400> SEQUENCE: 60

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 61
<211> LENGTH: 30
<212> TYPE: PRT
<213> ORGANISM: Homo sapiens

<400> SEQUENCE: 61

His Ala Asp Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 62
<211> LENGTH: 31
<212> TYPE: PRT
<213> ORGANISM: Homo sapiens

<400> SEQUENCE: 62

His Ala Asp Gly Thr Phe Thr Ser Asp Val Ser Ser Tyr Leu Glu Gly
 1               5                  10                  15
```

Gln Ala Ala Lys Glu Phe Ile Ala Trp Leu Val Lys Gly Arg Gly
            20                  25                  30

<210> SEQ ID NO 63
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 63

His Ala Asp Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg
            20                  25                  30

<210> SEQ ID NO 64
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 64

His Ala Asp Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Gly
            20                  25                  30

<210> SEQ ID NO 65
<211> LENGTH: 30
<212> TYPE: PRT
<213> ORGANISM: Homo sapiens

<400> SEQUENCE: 65

Tyr Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg
            20                  25                  30

<210> SEQ ID NO 66
<211> LENGTH: 31
<212> TYPE: PRT
<213> ORGANISM: Homo sapiens

<400> SEQUENCE: 66

Tyr Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Gly
            20                  25                  30

<210> SEQ ID NO 67
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 67

Tyr Ala Glu Gly Thr Phe Thr Ser Asp Val Ser Ser Tyr Leu Glu Gly
 1               5                  10                 15

Gln Ala Ala Lys Glu Phe Ile Ala Trp Leu Val Lys Gly Arg
            20                  25                  30

<210> SEQ ID NO 68
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<223> OTHER INFORMATION: this sequence has an amidated c-terminus

<400> SEQUENCE: 68

Tyr Ala Glu Gly Thr Phe Thr Ser Asp Val Ser Ser Tyr Leu Glu Gly
 1               5                  10                 15

Gln Ala Ala Lys Glu Phe Ile Ala Trp Leu Val Lys Gly Arg Gly
            20                  25                  30

<210> SEQ ID NO 69
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: N-acyl-histidine

<400> SEQUENCE: 69

Xaa Ala Glu Gly Thr Phe Thr Ser Asp Val Ser Ser Tyr Leu Glu Gly
 1               5                  10                 15

Gln Ala Ala Lys Glu Phe Ile Ala Trp Leu Val Lys Gly Arg
            20                  25                  30

<210> SEQ ID NO 70
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: N-acyl-histidine

<400> SEQUENCE: 70

Xaa Ala Glu Gly Thr Phe Thr Ser Asp Val Ser Ser Tyr Leu Glu Gly
 1               5                  10                 15

Gln Ala Ala Lys Glu Phe Ile Ala Trp Leu Val Lys Gly Arg Gly
            20                  25                  30

<210> SEQ ID NO 71
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: N-acyl-histidine
<220> FEATURE:
<223> OTHER INFORMATION: this sequence has an amidated c-terminus

<400> SEQUENCE: 71

-continued

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 72
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: N-acyl-histidine
<220> FEATURE:
<223> OTHER INFORMATION: this sequence has an amidated c-terminus

<400> SEQUENCE: 72

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 73
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: N-alkyl-histidine

<400> SEQUENCE: 73

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 74
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: N-alkyl-histidine

<400> SEQUENCE: 74

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 75
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)

-continued

```
<223> OTHER INFORMATION: N-alkyl-histidine
<220> FEATURE:
<223> OTHER INFORMATION: this sequence has an amidated c-terminus

<400> SEQUENCE: 75

Xaa Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg
             20                  25                  30

<210> SEQ ID NO 76
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: N-alkyl-histidine
<220> FEATURE:
<223> OTHER INFORMATION: this sequence has an amidated c-terminus

<400> SEQUENCE: 76

Xaa Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Gly
             20                  25                  30

<210> SEQ ID NO 77
<211> LENGTH: 29
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: N-methyl-alanine

<400> SEQUENCE: 77

Xaa Glu Gly Thr Phe Thr Ser Asp Val Ser Ser Tyr Leu Glu Gly Gln
  1               5                  10                  15

Ala Ala Lys Glu Phe Ile Ala Trp Leu Val Lys Gly Arg
             20                  25

<210> SEQ ID NO 78
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: N-methyl-alanine

<400> SEQUENCE: 78

Xaa Glu Gly Thr Phe Thr Ser Asp Val Ser Ser Tyr Leu Glu Gly Gln
  1               5                  10                  15

Ala Ala Lys Glu Phe Ile Ala Trp Leu Val Lys Gly Arg Gly
             20                  25                  30

<210> SEQ ID NO 79
<211> LENGTH: 30
<212> TYPE: PRT
<213> ORGANISM: Homo sapiens
```

-continued

<400> SEQUENCE: 79

His Ala Glu Gly Thr Phe Thr Ser Glu Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 80
<211> LENGTH: 31
<212> TYPE: PRT
<213> ORGANISM: Homo sapiens

<400> SEQUENCE: 80

His Ala Glu Gly Thr Phe Thr Ser Glu Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 81
<211> LENGTH: 30
<212> TYPE: PRT
<213> ORGANISM: Homo sapiens

<400> SEQUENCE: 81

His Ala Glu Gly Thr Phe Thr Ser Asp Val Ser Ser Tyr Leu Glu Gly
1               5                   10                  15

Gln Ala Ala Lys Glu Phe Ile Ala Phe Leu Val Lys Gly Arg
            20                  25                  30

<210> SEQ ID NO 82
<211> LENGTH: 31
<212> TYPE: PRT
<213> ORGANISM: Homo sapiens

<400> SEQUENCE: 82

His Ala Glu Gly Thr Phe Thr Ser Asp Val Ser Ser Tyr Leu Glu Gly
1               5                   10                  15

Gln Ala Ala Lys Glu Phe Ile Ala Phe Leu Val Lys Gly Arg Gly
            20                  25                  30

<210> SEQ ID NO 83
<211> LENGTH: 29
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<223> OTHER INFORMATION: this sequence has an amidated c-terminus

<400> SEQUENCE: 83

His Ala Glu Gly Thr Phe Thr Ser Asp Val Ser Ala Xaa Leu Glu Gly
1               5                   10                  15

Ala Ala Ala Lys Ala Phe Ile Ala Xaa Leu Val Lys Gly
            20                  25

<210> SEQ ID NO 84

```
<211> LENGTH: 29
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<223> OTHER INFORMATION: this sequence has an amidated c-terminus

<400> SEQUENCE: 84

His Ala Glu Gly Thr Phe Thr Ser Asp Ala Ser Ser Xaa Leu Glu Gly
 1               5                  10                  15

Ala Ala Ala Lys Ala Phe Ile Ala Xaa Leu Val Lys Gly
            20                  25

<210> SEQ ID NO 85
<211> LENGTH: 29
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<223> OTHER INFORMATION: this sequence has an amidated c-terminus

<400> SEQUENCE: 85

His Ala Glu Gly Thr Phe Thr Ala Asp Val Ser Ser Xaa Leu Glu Gly
 1               5                  10                  15

Ala Ala Ala Lys Ala Phe Ile Ala Xaa Leu Val Lys Gly
            20                  25

<210> SEQ ID NO 86
<211> LENGTH: 29
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<223> OTHER INFORMATION: this sequence has an amidated c-terminus

<400> SEQUENCE: 86

His Ala Glu Gly Thr Phe Thr Ser Asp Val Ser Ser Xaa Leu Glu Ala
 1               5                  10                  15

Ala Ala Ala Lys Ala Phe Ile Ala Xaa Leu Val Lys Gly
            20                  25

<210> SEQ ID NO 87
<211> LENGTH: 30
```

```
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: 3-(p-hydroxyphenyl)propionic acid
<220> FEATURE:
<223> OTHER INFORMATION: this sequence has an amidated c-terminus

<400> SEQUENCE: 87

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 88
<211> LENGTH: 29
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<223> OTHER INFORMATION: this sequence has an amidated c-terminus

<400> SEQUENCE: 88

His Ala Glu Gly Thr Phe Thr Ser Ala Val Ser Ser Xaa Leu Glu Gly
 1               5                  10                  15

Ala Ala Ala Lys Ala Phe Ile Ala Xaa Leu Val Lys Gly
            20                  25

<210> SEQ ID NO 89
<211> LENGTH: 29
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<223> OTHER INFORMATION: this sequence has an amidated c-terminus

<400> SEQUENCE: 89

His Ala Glu Gly Thr Phe Thr Ser Asp Val Ala Ser Xaa Leu Glu Gly
 1               5                  10                  15

Ala Ala Ala Lys Ala Phe Ile Ala Xaa Leu Val Lys Gly
            20                  25

<210> SEQ ID NO 90
<211> LENGTH: 28
<212> TYPE: PRT
<213> ORGANISM: Artificial Sequence
<220> FEATURE:
<223> OTHER INFORMATION: Description of Artificial Sequence: Mutagen
<220> FEATURE:
```

```
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (28)
<223> OTHER INFORMATION: gamma-aminobutyric acid
<220> FEATURE:
<223> OTHER INFORMATION: this sequence has an amidated c-terminus

<400> SEQUENCE: 90

His Ala Glu Gly Thr Phe Thr Ser Asp Val Ser Ser Xaa Leu Glu Ala
 1               5                  10                  15

Ala Ala Ala Lys Ala Phe Ile Ala Xaa Leu Val Xaa
            20                  25

<210> SEQ ID NO 91
<211> LENGTH: 28
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (28)
<223> OTHER INFORMATION: gamma-aminobutyric acid
<220> FEATURE:
<223> OTHER INFORMATION: this sequence has an amidated c-terminus

<400> SEQUENCE: 91

His Ala Glu Gly Thr Phe Thr Ser Ala Val Ser Ser Xaa Leu Glu Ala
 1               5                  10                  15

Ala Ala Ala Lys Ala Phe Ile Ala Xaa Leu Val Xaa
            20                  25

<210> SEQ ID NO 92
<211> LENGTH: 28
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (28)
<223> OTHER INFORMATION: gamma-aminobutyric acid
<220> FEATURE:
<223> OTHER INFORMATION: this sequence has an amidated c-terminus

<400> SEQUENCE: 92

His Ala Glu Gly Thr Phe Thr Ser Asp Val Ala Ser Xaa Leu Glu Ala
 1               5                  10                  15
```

-continued

Ala Ala Ala Lys Ala Phe Ile Ala Xaa Leu Val Xaa
            20                  25

<210> SEQ ID NO 93
<211> LENGTH: 28
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (28)
<223> OTHER INFORMATION: gamma-aminobutyric acid
<220> FEATURE:
<223> OTHER INFORMATION: this sequence has an amidated c-terminus

<400> SEQUENCE: 93

His Ala Glu Gly Thr Phe Thr Ser Asp Val Ser Ala Xaa Leu Glu Ala
 1               5                  10                  15

Ala Ala Ala Lys Ala Phe Ile Ala Xaa Leu Val Xaa
            20                  25

<210> SEQ ID NO 94
<211> LENGTH: 28
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (28)
<223> OTHER INFORMATION: gamma-aminobutyric acid
<220> FEATURE:
<223> OTHER INFORMATION: this sequence has an amidated c-terminus

<400> SEQUENCE: 94

His Ala Glu Gly Thr Phe Thr Ser Asp Val Ser Ser Xaa Leu Ala Ala
 1               5                  10                  15

Ala Ala Ala Lys Ala Phe Ile Ala Xaa Leu Val Xaa
            20                  25

<210> SEQ ID NO 95
<211> LENGTH: 28
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:

```
<221> NAME/KEY: MOD_RES
<222> LOCATION: (28)
<223> OTHER INFORMATION: gamma-aminobutyric acid
<220> FEATURE:
<223> OTHER INFORMATION: this sequence has an amidated c-terminus

<400> SEQUENCE: 95

His Ala Glu Gly Thr Phe Thr Ser Asp Val Ser Ser Xaa Leu Glu Ala
 1               5                  10                  15

Ala Ala Ala Ala Ala Phe Ile Ala Xaa Leu Val Xaa
            20                  25

<210> SEQ ID NO 96
<211> LENGTH: 28
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (28)
<223> OTHER INFORMATION: gamma-aminobutyric acid
<220> FEATURE:
<223> OTHER INFORMATION: this sequence has an amidated c-terminus

<400> SEQUENCE: 96

His Ala Glu Gly Thr Phe Thr Ser Asp Val Ser Ser Xaa Leu Glu Ala
 1               5                  10                  15

Ala Ala Ala Lys Ala Phe Ile Ala Xaa Ala Val Xaa
            20                  25

<210> SEQ ID NO 97
<211> LENGTH: 27
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (27)
<223> OTHER INFORMATION: gamma-aminobutyric acid
<220> FEATURE:
<223> OTHER INFORMATION: this sequence has an amidated c-terminus

<400> SEQUENCE: 97

His Ala Glu Gly Thr Phe Thr Ser Asp Val Ser Ser Xaa Leu Glu Ala
 1               5                  10                  15

Ala Ala Ala Ala Ala Phe Ile Ala Xaa Leu Xaa
            20                  25

<210> SEQ ID NO 98
<211> LENGTH: 27
<212> TYPE: PRT
<213> ORGANISM: Artificial Sequence
```

```
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (27)
<223> OTHER INFORMATION: gamma-aminobutyric acid
<220> FEATURE:
<223> OTHER INFORMATION: this sequence has an amidated c-terminus

<400> SEQUENCE: 98

His Ala Glu Gly Thr Phe Thr Ser Asp Val Ser Ser Xaa Leu Glu Ala
 1               5                  10                  15

Ala Ala Ala Lys Ala Phe Ile Ala Ala Leu Xaa
            20                  25

<210> SEQ ID NO 99
<211> LENGTH: 27
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (27)
<223> OTHER INFORMATION: gamma-aminobutyric acid
<220> FEATURE:
<223> OTHER INFORMATION: this sequence has an amidated c-terminus

<400> SEQUENCE: 99

His Ala Glu Gly Thr Phe Thr Ser Asp Val Ser Ser Xaa Leu Glu Ala
 1               5                  10                  15

Ala Ala Ala Lys Ala Ala Ile Ala Xaa Leu Xaa
            20                  25

<210> SEQ ID NO 100
<211> LENGTH: 27
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (27)
<223> OTHER INFORMATION: gamma-aminobutyric acid
<220> FEATURE:
<223> OTHER INFORMATION: this sequence has an amidated c-terminus

<400> SEQUENCE: 100
```

-continued

```
His Ala Glu Gly Thr Phe Thr Ser Asp Val Ser Ser Xaa Leu Glu Ala
  1               5                  10                  15

Ala Ala Ala Lys Ala Phe Ala Ala Xaa Leu Xaa
             20                  25
```

<210> SEQ ID NO 101
<211> LENGTH: 27
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (27)
<223> OTHER INFORMATION: gamma-aminobutyric acid
<220> FEATURE:
<223> OTHER INFORMATION: this sequence has an amidated c-terminus

<400> SEQUENCE: 101

```
His Ala Glu Gly Thr Phe Thr Ser Asp Val Ser Ser Xaa Leu Glu Gly
  1               5                  10                  15

Ala Ala Ala Lys Ala Phe Ile Ala Xaa Leu Xaa
             20                  25
```

<210> SEQ ID NO 102
<211> LENGTH: 27
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (27)
<223> OTHER INFORMATION: gamma-aminobutyric acid
<220> FEATURE:
<223> OTHER INFORMATION: this sequence has an amidated c-terminus

<400> SEQUENCE: 102

```
His Ala Glu Gly Thr Phe Thr Ser Asp Val Ser Ser Xaa Ala Glu Ala
  1               5                  10                  15

Ala Ala Ala Lys Ala Phe Ile Ala Xaa Leu Xaa
             20                  25
```

<210> SEQ ID NO 103
<211> LENGTH: 27
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES

```
<222> LOCATION: (25)
<223> OTHER INFORMATION: beta-(3-pyridinyl)alanine
<220> FEATURE:
<221> NAME/KEY: MOD_RES
<222> LOCATION: (27)
<223> OTHER INFORMATION: gamma-aminobutyric acid
<220> FEATURE:
<223> OTHER INFORMATION: this sequence has an amidated c-terminus

<400> SEQUENCE: 103

His Ala Glu Gly Thr Phe Thr Ser Asp Val Ser Ser Xaa Leu Glu Ala
 1               5                  10                  15

Ala Ala Ala Lys Ala Phe Ile Ala Xaa Leu Xaa
            20                  25

<210> SEQ ID NO 104
<211> LENGTH: 27
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (27)
<223> OTHER INFORMATION: gamma-aminobutyric acid
<220> FEATURE:
<223> OTHER INFORMATION: this sequence has an amidated c-terminus

<400> SEQUENCE: 104

His Ala Glu Gly Thr Phe Thr Ser Asp Val Ala Ser Xaa Leu Glu Ala
 1               5                  10                  15

Ala Ala Ala Lys Ala Phe Ile Ala Xaa Leu Xaa
            20                  25

<210> SEQ ID NO 105
<211> LENGTH: 28
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (20)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<223> OTHER INFORMATION: this sequence has an amidated c-terminus

<400> SEQUENCE: 105

His Ala Glu Gly Thr Phe Thr Ser Asp Val Ala Ser Xaa Leu Glu Gly
 1               5                  10                  15

Ala Ala Ala Xaa Ala Phe Ile Ala Xaa Leu Val Lys
            20                  25

<210> SEQ ID NO 106
```

```
<211> LENGTH: 28
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<223> OTHER INFORMATION: this sequence has an amidated c-terminus

<400> SEQUENCE: 106

His Ala Glu Gly Thr Phe Thr Ser Asp Val Ala Ser Xaa Leu Glu Gly
 1               5                  10                  15

Ala Ala Ala Lys Ala Phe Ile Ala Xaa Leu Val Lys
            20                  25

<210> SEQ ID NO 107
<211> LENGTH: 28
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (28)
<223> OTHER INFORMATION: gamma-aminobutyric acid
<220> FEATURE:
<223> OTHER INFORMATION: this sequence has an amidated c-terminus

<400> SEQUENCE: 107

His Xaa Glu Gly Thr Phe Thr Ser Asp Val Ala Ser Xaa Leu Glu Gly
 1               5                  10                  15

Ala Ala Ala Lys Ala Phe Ile Ala Xaa Leu Val Xaa
            20                  25

<210> SEQ ID NO 108
<211> LENGTH: 27
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<223> OTHER INFORMATION: this sequence has an amidated c-terminus
```

```
<400> SEQUENCE: 108

His Xaa Glu Gly Thr Phe Thr Ser Asp Val Ala Ser Xaa Leu Glu Ala
 1               5                   10                  15

Ala Ala Ala Lys Ala Phe Ile Ala Xaa Leu Val
            20                  25

<210> SEQ ID NO 109
<211> LENGTH: 28
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (28)
<223> OTHER INFORMATION: gamma-aminobutyric acid
<220> FEATURE:
<223> OTHER INFORMATION: this sequence has an amidated c-terminus

<400> SEQUENCE: 109

His Ala Glu Gly Thr Phe Thr Ser Asp Val Ala Ala Xaa Leu Glu Gly
 1               5                   10                  15

Ala Ala Ala Lys Ala Phe Ile Ala Xaa Leu Val Xaa
            20                  25

<210> SEQ ID NO 110
<211> LENGTH: 28
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (27)
<223> OTHER INFORMATION: tert-butylglycine
<220> FEATURE:
<221> NAME/KEY: MOD_RES
<222> LOCATION: (28)
<223> OTHER INFORMATION: gamma-aminobutyric acid
<220> FEATURE:
<223> OTHER INFORMATION: this sequence has an amidated c-terminus

<400> SEQUENCE: 110

His Ala Glu Gly Thr Phe Thr Ser Asp Val Ala Ser Xaa Leu Glu Gly
 1               5                   10                  15

Ala Ala Ala Lys Ala Phe Ile Ala Xaa Leu Xaa Xaa
            20                  25

<210> SEQ ID NO 111
<211> LENGTH: 28
<212> TYPE: PRT
<213> ORGANISM: Artificial Sequence
<220> FEATURE:
```

<223> OTHER INFORMATION: Description of Artificial Sequence: Mutagen
<220> FEATURE:
<221> NAME/KEY: MOD_RES
<222> LOCATION: (10)
<223> OTHER INFORMATION: tert-butylglycine
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<221> NAME/KEY: MOD_RES
<222> LOCATION: (28)
<223> OTHER INFORMATION: gamma-aminobutyric acid
<220> FEATURE:
<223> OTHER INFORMATION: this sequence has an amidated c-terminus

<400> SEQUENCE: 111

His Ala Glu Gly Thr Phe Thr Ser Asp Xaa Ala Ser Xaa Leu Glu Gly
 1               5                  10                  15

Ala Ala Ala Lys Ala Phe Ile Ala Xaa Leu Val Xaa
            20                  25

<210> SEQ ID NO 112
<211> LENGTH: 27
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (25)
<223> OTHER INFORMATION: beta-(3-pyridinyl)alanine
<220> FEATURE:
<223> OTHER INFORMATION: this sequence has an amidated c-terminus

<400> SEQUENCE: 112

His Xaa Glu Gly Thr Phe Thr Ser Asp Val Ala Ala Xaa Leu Glu Ala
 1               5                  10                  15

Ala Ala Ala Lys Ala Phe Ile Ala Xaa Leu Val
            20                  25

<210> SEQ ID NO 113
<211> LENGTH: 28
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (10)
<223> OTHER INFORMATION: tert-butylglycine
<220> FEATURE:
<221> NAME/KEY: MOD_RES
<222> LOCATION: (13)
<223> OTHER INFORMATION: beta-(3-pyridinyl)alanine
<220> FEATURE:
<221> NAME/KEY: MOD_RES
<222> LOCATION: (14)
<223> OTHER INFORMATION: tert-butylglycine
<220> FEATURE:
<221> NAME/KEY: MOD_RES

```
<222> LOCATION: (25)
<223> OTHER INFORMATION: beta-(3-pyridinyl)alanine
<220> FEATURE:
<221> NAME/KEY: MOD_RES
<222> LOCATION: (28)
<223> OTHER INFORMATION: gamma-aminobutyric acid
<220> FEATURE:
<223> OTHER INFORMATION: this sequence has an amidated c-terminus

<400> SEQUENCE: 113

His Ala Glu Gly Thr Phe Thr Ser Asp Xaa Ala Ala Xaa Xaa Glu Ala
 1               5                  10                  15

Ala Ala Ala Lys Ala Phe Ile Ala Xaa Leu Val Xaa
            20                  25

<210> SEQ ID NO 114
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 114

His Xaa Glu Gly Thr Phe Thr Ser Asp Val Ser Ser Tyr Leu Glu Gly
 1               5                  10                  15

Gln Ala Ala Lys Glu Phe Ile Ala Trp Xaa Val Lys Gly Arg
            20                  25                  30

<210> SEQ ID NO 115
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (14)
<223> OTHER INFORMATION: 1-amino-1-cyclohexanecarboxylic acid
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 115

His Ala Glu Gly Thr Phe Thr Ser Asp Val Ser Ser Tyr Xaa Glu Gly
 1               5                  10                  15

Gln Ala Ala Lys Glu Phe Ile Ala Trp Xaa Val Lys Gly Arg
            20                  25                  30

<210> SEQ ID NO 116
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
```

<223> OTHER INFORMATION: alpha-aminoisobutyric acid
<220> FEATURE:
<223> OTHER INFORMATION: this sequence has an amidated c-terminus

<400> SEQUENCE: 116

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 117
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: N,N-tetramethylamidinohistidine
<220> FEATURE:
<223> OTHER INFORMATION: this sequence has an amidated c-terminus

<400> SEQUENCE: 117

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 118
<211> LENGTH: 29
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 118

Xaa Glu Gly Thr Phe Thr Ser Asp Val Ser Ser Tyr Leu Glu Gly Gln
 1               5                  10                  15

Ala Ala Lys Glu Phe Ile Ala Trp Leu Val Lys Gly Arg
            20                  25

<210> SEQ ID NO 119
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 119

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

```
<210> SEQ ID NO 120
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (10)
<223> OTHER INFORMATION: 1-amino-1-cyclohexanecarboxylic acid
<220> FEATURE:
<221> NAME/KEY: MOD_RES
<222> LOCATION: (14)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 120

His Ala Glu Gly Thr Phe Thr Ser Asp Xaa Ser Ser Tyr Xaa Glu Gly
 1               5                  10                  15

Gln Ala Ala Lys Glu Phe Ile Ala Trp Leu Val Lys Gly Arg
            20                  25                  30

<210> SEQ ID NO 121
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (23)
<223> OTHER INFORMATION: 1-amino-1-cyclohexanecarboxylic acid
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 121

His Ala Glu Gly Thr Phe Thr Ser Asp Val Ser Ser Tyr Leu Glu Gly
 1               5                  10                  15

Gln Ala Ala Lys Glu Phe Xaa Ala Trp Xaa Val Lys Gly Arg
            20                  25                  30

<210> SEQ ID NO 122
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (14)
<223> OTHER INFORMATION: 1-amino-1-cyclohexanecarboxylic acid
<220> FEATURE:
<221> NAME/KEY: MOD_RES
<222> LOCATION: (18)
<223> OTHER INFORMATION: alpha-aminoisobutyric acid
<220> FEATURE:
<223> OTHER INFORMATION: this sequence has an amidated c-terminus

<400> SEQUENCE: 122

His Ala Glu Gly Thr Phe Thr Ser Asp Val Ser Ser Tyr Xaa Glu Gly
 1               5                  10                  15

Gln Xaa Ala Lys Glu Phe Ile Ala Trp Leu Val Lys Gly Arg
            20                  25                  30

<210> SEQ ID NO 123
```

```
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (18)
<223> OTHER INFORMATION: alpha-aminoisobutyric acid
<220> FEATURE:
<221> NAME/KEY: MOD_RES
<222> LOCATION: (23)
<223> OTHER INFORMATION: 1-amino-1-cyclohexanecarboxylic acid
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 123

His Ala Glu Gly Thr Phe Thr Ser Asp Val Ser Ser Tyr Leu Glu Gly
 1               5                  10                  15

Gln Xaa Ala Lys Glu Phe Xaa Ala Trp Xaa Val Lys Gly Arg
            20                  25                  30

<210> SEQ ID NO 124
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (10))
<223> OTHER INFORMATION: 1-amino-1-cyclohexanecarboxylic acid
<220> FEATURE:
<221> NAME/KEY: MOD_RES
<222> LOCATION: (23)
<223> OTHER INFORMATION: 1-amino-1-cyclohexanecarboxylic acid
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 124

His Ala Glu Gly Thr Phe Thr Ser Asp Xaa Ser Ser Tyr Leu Glu Gly
 1               5                  10                  15

Gln Ala Ala Lys Glu Phe Xaa Ala Trp Xaa Val Lys Gly Arg
            20                  25                  30

<210> SEQ ID NO 125
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: urocanic acid
<220> FEATURE:
<223> OTHER INFORMATION: this sequence has an amidated c-terminus

<400> SEQUENCE: 125

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30
```

<210> SEQ ID NO 126
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: trans-3-(3-pyridyl)acrylic acid
<220> FEATURE:
<223> OTHER INFORMATION: this sequence has an amidated c-terminus

<400> SEQUENCE: 126

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 127
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: (4-pyridylthio)acetic acid
<220> FEATURE:
<223> OTHER INFORMATION: this sequence has an amidated c-terminus

<400> SEQUENCE: 127

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 128
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: N-methylalanine
<220> FEATURE:
<223> OTHER INFORMATION: this sequence has an amidated c-terminus

<400> SEQUENCE: 128

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 129
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: N-methylglycine
<220> FEATURE:

<223> OTHER INFORMATION: this sequence has an amidated c-terminus

<400> SEQUENCE: 129

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 130
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: 1-amino-1-cyclopentanecarboxylic acid

<400> SEQUENCE: 130

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 131
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (3)
<223> OTHER INFORMATION: N-methylglutamic acid
<220> FEATURE:
<223> OTHER INFORMATION: this sequence has an amidated c-terminus

<400> SEQUENCE: 131

His Ala Xaa Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 132
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: 1-amino-1-cyclopentanecarboxylic acid
<220> FEATURE:
<221> NAME/KEY: MOD_RES
<222> LOCATION: (14)
<223> OTHER INFORMATION: 1-amino-1-cyclohexanecarboxylic acid
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 132

His Xaa Glu Gly Thr Phe Thr Ser Asp Val Ser Ser Tyr Xaa Glu Gly
 1               5                  10                  15

```
Gln Ala Ala Lys Glu Phe Ile Ala Trp Xaa Val Lys Gly Arg
            20                  25                  30

<210> SEQ ID NO 133
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 133

His Xaa Glu Gly Thr Phe Thr Ser Asp Val Ser Ser Tyr Leu Glu Gly
 1               5                  10                  15

Gln Ala Ala Lys Glu Phe Ile Ala Trp Xaa Val Lys Gly Arg
            20                  25                  30

<210> SEQ ID NO 134
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (19)
<223> OTHER INFORMATION: alpha-aminoisobutyric acid
<220> FEATURE:
<223> OTHER INFORMATION: this sequence has an amidated c-terminus

<400> SEQUENCE: 134

His Xaa Glu Gly Thr Phe Thr Ser Asp Val Ser Ser Tyr Leu Glu Gly
 1               5                  10                  15

Gln Ala Xaa Lys Glu Phe Ile Ala Trp Leu Val Lys Gly Arg
            20                  25                  30

<210> SEQ ID NO 135
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (18)
<223> OTHER INFORMATION: alpha-aminoisobutyric acid
<220> FEATURE:
<223> OTHER INFORMATION: this sequence has an amidated c-terminus

<400> SEQUENCE: 135

His Xaa Glu Gly Thr Phe Thr Ser Asp Val Ser Ser Tyr Leu Glu Gly
 1               5                  10                  15

Gln Xaa Ala Lys Glu Phe Ile Ala Trp Leu Val Lys Gly Arg
            20                  25                  30
```

<210> SEQ ID NO 136
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (24)
<223> OTHER INFORMATION: alpha-aminoisobutyric acid
<220> FEATURE:
<223> OTHER INFORMATION: this sequence has an amidated c-terminus

<400> SEQUENCE: 136

His Xaa Glu Gly Thr Phe Thr Ser Asp Val Ser Ser Tyr Leu Glu Gly
 1               5                  10                  15

Gln Ala Ala Lys Glu Phe Ile Xaa Trp Leu Val Lys Gly Arg
             20                  25                  30

<210> SEQ ID NO 137
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (14)
<223> OTHER INFORMATION: cyclohexylalanine
<220> FEATURE:
<223> OTHER INFORMATION: this sequence has an amidated c-terminus

<400> SEQUENCE: 137

His Xaa Glu Gly Thr Phe Thr Ser Asp Val Ser Ser Tyr Xaa Glu Gly
 1               5                  10                  15

Gln Ala Ala Lys Glu Phe Ile Ala Trp Leu Val Lys Gly Arg
             20                  25                  30

<210> SEQ ID NO 138
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (26)
<223> OTHER INFORMATION: cyclohexylalanine
<220> FEATURE:
<223> OTHER INFORMATION: this sequence has an amidated c-terminus

<400> SEQUENCE: 138

His Xaa Glu Gly Thr Phe Thr Ser Asp Val Ser Ser Tyr Leu Glu Gly
 1               5                  10                  15

Gln Ala Ala Lys Glu Phe Ile Ala Trp Xaa Val Lys Gly Arg
             20                  25                  30

```
<210> SEQ ID NO 139
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<223> OTHER INFORMATION: this sequence has an amidated c-terminus

<400> SEQUENCE: 139

His Xaa Glu Gly Thr Phe Thr Ser Asp Val Ser Ser Tyr Leu Glu Gly
 1               5                  10                  15

Glu Ala Ala Lys Glu Phe Ile Ala Trp Leu Val Lys Gly Arg
            20                  25                  30

<210> SEQ ID NO 140
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (14)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 140

His Xaa Glu Gly Thr Phe Thr Ser Asp Val Ser Ser Tyr Xaa Glu Gly
 1               5                  10                  15

Gln Ala Ala Lys Glu Phe Ile Ala Trp Leu Val Lys Gly Arg
            20                  25                  30

<210> SEQ ID NO 141
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (14)
<223> OTHER INFORMATION: 1-amino-1-cyclohexanecarboxylic acid
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 141

His Xaa Glu Gly Thr Phe Thr Ser Asp Val Ser Ser Tyr Xaa Glu Gly
 1               5                  10                  15

Gln Ala Ala Lys Glu Phe Ile Ala Trp Xaa Val Lys Gly Arg
            20                  25                  30
```

```
<210> SEQ ID NO 142
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (16)
<223> OTHER INFORMATION: alpha-aminoisobutyric acid
<220> FEATURE:
<223> OTHER INFORMATION: this sequence has an amidated c-terminus

<400> SEQUENCE: 142

His Xaa Glu Gly Thr Phe Thr Ser Asp Val Ser Ser Tyr Leu Glu Xaa
  1               5                  10                  15

Gln Ala Ala Lys Glu Phe Ile Ala Trp Leu Val Lys Gly Arg
             20                  25                  30

<210> SEQ ID NO 143
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (16)
<223> OTHER INFORMATION: beta alanine
<220> FEATURE:
<223> OTHER INFORMATION: this sequence has an amidated c-terminus

<400> SEQUENCE: 143

His Xaa Glu Gly Thr Phe Thr Ser Asp Val Ser Ser Tyr Leu Glu Xaa
  1               5                  10                  15

Gln Ala Ala Lys Glu Phe Ile Ala Trp Leu Val Lys Gly Arg
             20                  25                  30

<210> SEQ ID NO 144
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<223> OTHER INFORMATION: this sequence has an amidated c-terminus

<400> SEQUENCE: 144

His Xaa Glu Gly Thr Phe Thr Ser Asp Val Ser Ser Tyr Leu Glu Gly
  1               5                  10                  15

Gln Ala Lys Lys Glu Phe Ile Ala Trp Leu Val Lys Gly Arg
             20                  25                  30

<210> SEQ ID NO 145
<211> LENGTH: 30
<212> TYPE: PRT
<213> ORGANISM: Artificial Sequence
```

```
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (6)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 145

His Xaa Glu Gly Thr Xaa Thr Ser Asp Val Ser Ser Tyr Leu Glu Gly
  1               5                  10                  15

Gln Ala Ala Lys Glu Phe Ile Ala Trp Leu Val Lys Gly Arg
             20                  25                  30

<210> SEQ ID NO 146
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (23)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 146

His Xaa Glu Gly Thr Phe Thr Ser Asp Val Ser Ser Tyr Leu Glu Gly
  1               5                  10                  15

Gln Ala Ala Lys Glu Phe Xaa Ala Trp Leu Val Lys Gly Arg
             20                  25                  30

<210> SEQ ID NO 147
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (27)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 147

His Xaa Glu Gly Thr Phe Thr Ser Asp Val Ser Ser Tyr Leu Glu Gly
  1               5                  10                  15

Gln Ala Ala Lys Glu Phe Ile Ala Trp Leu Xaa Lys Gly Arg
             20                  25                  30

<210> SEQ ID NO 148
<211> LENGTH: 30
<212> TYPE: PRT
<213> ORGANISM: Artificial Sequence
<220> FEATURE:
```

```
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (8)
<223> OTHER INFORMATION: alpha-aminoisobutyric acid
<220> FEATURE:
<223> OTHER INFORMATION: this sequence has an amidated c-terminus

<400> SEQUENCE: 148

His Xaa Glu Gly Thr Phe Thr Xaa Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 149
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (12)
<223> OTHER INFORMATION: alpha-aminoisobutyric acid
<220> FEATURE:
<223> OTHER INFORMATION: this sequence has an amidated c-terminus

<400> SEQUENCE: 149

His Xaa Glu Gly Thr Phe Thr Ser Asp Val Ser Xaa Tyr Leu Glu Gly
 1               5                  10                  15

Gln Ala Ala Lys Glu Phe Ile Ala Trp Leu Val Lys Gly Arg
            20                  25                  30

<210> SEQ ID NO 150
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (11)
<223> OTHER INFORMATION: alpha-aminoisobutyric acid
<220> FEATURE:
<223> OTHER INFORMATION: this sequence has an amidated c-terminus

<400> SEQUENCE: 150

His Xaa Glu Gly Thr Phe Thr Ser Asp Val Xaa Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 151
<211> LENGTH: 30
<212> TYPE: PRT
<213> ORGANISM: Artificial Sequence
<220> FEATURE:
<223> OTHER INFORMATION: Description of Artificial Sequence: Mutagen
```

```
<220> FEATURE:
<221> NAME/KEY: MOD_RES
<222> LOCATION: (13)
<223> OTHER INFORMATION: [125I]-3-iodotyrosine

<400> SEQUENCE: 151

His Ala Glu Gly Thr Phe Thr Ser Asp Val Ser Ser Xaa Leu Glu Gly
 1               5                  10                  15

Gln Ala Ala Lys Glu Phe Ile Ala Trp Leu Val Lys Gly Arg
            20                  25                  30

<210> SEQ ID NO 152
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MUTAGEN
<222> LOCATION: (1)...(1)
<223> OTHER INFORMATION: N-alpha-(4-(2-hydroxyethyl)-1-piperazine-
      ethanesulfonyl)-histidine
<220> FEATURE:
<223> OTHER INFORMATION: this sequence has an amidated c-terminus

<400> SEQUENCE: 152

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 153
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (1)
<223> OTHER INFORMATION: N-alpha-(4-(2-hydroxyethyl)-1-piperazine-
      acetyl)-histidine
<220> FEATURE:
<223> OTHER INFORMATION: this sequence has an amidated c-terminus

<400> SEQUENCE: 153

Xaa Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 154
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (27)
<223> OTHER INFORMATION: 1-amino-1-cyclopentancarboxylic acid
<220> FEATURE:
<223> OTHER INFORMATION: this sequence has an amidated c-terminus

<400> SEQUENCE: 154
```

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Xaa Lys Gly Arg
            20                  25                  30

<210> SEQ ID NO 155
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<221> NAME/KEY: MOD_RES
<222> LOCATION: (30)
<223> OTHER INFORMATION: N-epsilon-tetradecanoyl-lysine
<220> FEATURE:
<223> OTHER INFORMATION: this sequence has an amidated c-terminus

<400> SEQUENCE: 155

His Xaa Glu Gly Thr Phe Thr Ser Asp Val Ser Ser Tyr Leu Glu Gly
 1               5                  10                  15

Gln Ala Ala Lys Glu Phe Ile Ala Trp Xaa Val Lys Gly Xaa
            20                  25                  30

<210> SEQ ID NO 156
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<221> NAME/KEY: MOD_RES
<222> LOCATION: (30)
<223> OTHER INFORMATION: N-epsilon-tetradecanoyl-lysine
<220> FEATURE:
<223> OTHER INFORMATION: this sequence has an amidated c-terminus

<400> SEQUENCE: 156

His Xaa Glu Gly Thr Phe Thr Ser Asp Val Ser Ser Tyr Leu Glu Gly
 1               5                  10                  15

Gln Ala Ala Arg Glu Phe Ile Ala Trp Xaa Val Arg Gly Xaa
            20                  25                  30

<210> SEQ ID NO 157
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES

```
<222> LOCATION: (26)
<223> OTHER INFORMATION: 1-amino-1-cyclohexanecarboxylic acid
<220> FEATURE:
<221> NAME/KEY: MOD_RES
<222> LOCATION: (28)
<223> OTHER INFORMATION: N-epsilon-tetradecanoyl-lysine
<220> FEATURE:
<223> OTHER INFORMATION: this sequence has an amidated c-terminus

<400> SEQUENCE: 157

His Xaa Glu Gly Thr Phe Thr Ser Asp Val Ser Ser Tyr Leu Glu Gly
 1               5                  10                  15

Gln Ala Ala Arg Glu Phe Ile Ala Trp Xaa Val Xaa Gly Arg
            20                  25                  30

<210> SEQ ID NO 158
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (20)
<223> OTHER INFORMATION: N-epsilon-tetradecanoyl-lysine
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<223> OTHER INFORMATION: this sequence has an amidated c-terminus

<400> SEQUENCE: 158

His Xaa Glu Gly Thr Phe Thr Ser Asp Val Ser Ser Tyr Leu Glu Gly
 1               5                  10                  15

Gln Ala Ala Xaa Glu Phe Ile Ala Trp Xaa Val Arg Gly Arg
            20                  25                  30

<210> SEQ ID NO 159
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (30)
<223> OTHER INFORMATION: N-epsilon-octanoyl-lysine
<220> FEATURE:
<223> OTHER INFORMATION: this sequence has an amidated c-terminus

<400> SEQUENCE: 159

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Xaa
            20                  25                  30

<210> SEQ ID NO 160
<211> LENGTH: 30
<212> TYPE: PRT
<213> ORGANISM: Artificial Sequence
<220> FEATURE:
```

```
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (14)
<223> OTHER INFORMATION: 1-amino-1-cyclohexanecarboxylic acid
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<221> NAME/KEY: MOD_RES
<222> LOCATION: (30)
<223> OTHER INFORMATION: N-epsilon-octanoyl-lysine
<220> FEATURE:
<223> OTHER INFORMATION: this sequence has an amidated c-terminus

<400> SEQUENCE: 160

His Xaa Glu Gly Thr Phe Thr Ser Asp Val Ser Ser Tyr Xaa Glu Gly
 1               5                  10                  15

Gln Ala Ala Lys Glu Phe Ile Ala Trp Xaa Val Lys Gly Xaa
            20                  25                  30

<210> SEQ ID NO 161
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<221> NAME/KEY: MOD_RES
<222> LOCATION: (30)
<223> OTHER INFORMATION: N-epsilon-tetradecanoyl-lysine

<400> SEQUENCE: 161

His Xaa Glu Gly Thr Phe Thr Ser Asp Val Ser Ser Tyr Leu Glu Gly
 1               5                  10                  15

Gln Ala Ala Arg Glu Phe Ile Ala Trp Xaa Val Arg Gly Xaa
            20                  25                  30

<210> SEQ ID NO 162
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<221> NAME/KEY: MOD_RES
<222> LOCATION: (28)
<223> OTHER INFORMATION: N-epsilon-tetradecanoyl-lysine

<400> SEQUENCE: 162

His Xaa Glu Gly Thr Phe Thr Ser Asp Val Ser Ser Tyr Leu Glu Gly
```

```
                1               5                  10                 15
Gln Ala Ala Arg Glu Phe Ile Ala Trp Xaa Val Xaa Gly Arg
                20                 25                 30

<210> SEQ ID NO 163
<211> LENGTH: 30
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (20)
<223> OTHER INFORMATION: N-epsilon-tetradecanoyl-lysine
<220> FEATURE:
<221> NAME/KEY: MOD_RES
<222> LOCATION: (26)
<223> OTHER INFORMATION: 1-amino-1-cyclohexanecarboxylic acid

<400> SEQUENCE: 163

His Xaa Glu Gly Thr Phe Thr Ser Asp Val Ser Ser Tyr Leu Glu Gly
  1               5                  10                 15

Gln Ala Ala Xaa Glu Phe Ile Ala Trp Xaa Val Arg Gly Arg
                20                 25                 30

<210> SEQ ID NO 164
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<221> NAME/KEY: MOD_RES
<222> LOCATION: (30)
<223> OTHER INFORMATION: N-epsilon-tetradecanoyl-lysine

<400> SEQUENCE: 164

His Xaa Glu Gly Thr Phe Thr Ser Asp Val Ser Ser Tyr Leu Glu Gly
  1               5                  10                 15

Gln Ala Ala Arg Glu Phe Ile Ala Trp Xaa Val Arg Gly Xaa Gly
                20                 25                 30

<210> SEQ ID NO 165
<211> LENGTH: 31
<212> TYPE: PRT
<213> ORGANISM: Artificial Sequence
<220> FEATURE:
<223> OTHER INFORMATION: Description of Artificial Sequence: Mutagen
<220> FEATURE:
<221> NAME/KEY: MOD_RES
<222> LOCATION: (2)
<223> OTHER INFORMATION: alpha-aminoisobutyric acid
<220> FEATURE:
<221> NAME/KEY: MOD_RES
<222> LOCATION: (26)
<223> OTHER INFORMATION: 1-amino-1-cyclohexanecarboxylic acid
<220> FEATURE:
<221> NAME/KEY: MOD_RES
<222> LOCATION: (28)
```

-continued

```
<223> OTHER INFORMATION: N-epsilon-tetradecanoyl-lysine

<400> SEQUENCE: 165

His Xaa Glu Gly Thr Phe Thr Ser Asp Val Ser Ser Tyr Leu Glu Gly
 1               5                  10                  15

Gln Ala Ala Arg Glu Phe Ile Ala Trp Xaa Val Xaa Gly Arg Gly
            20                  25                  30
```